US009803189B2

(12) United States Patent
Peabody et al.

(10) Patent No.: US 9,803,189 B2
(45) Date of Patent: Oct. 31, 2017

(54) VIRUS-LIKE PLATFORM FOR RAPID VACCINE DISCOVERY

(75) Inventors: David S. Peabody, Albuquerque, NM (US); Bryce Chackerian, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 772 days.

(21) Appl. No.: 11/895,198

(22) Filed: Aug. 23, 2007

(65) Prior Publication Data

US 2009/0054246 A1   Feb. 26, 2009

Related U.S. Application Data

(60) Provisional application No. 60/839,619, filed on Aug. 23, 2006, provisional application No. 60/899,237, filed on Feb. 2, 2007.

(51) Int. Cl.

| C40B 40/02 | (2006.01) |
|---|---|
| C12N 15/10 | (2006.01) |
| C07K 14/005 | (2006.01) |
| A61K 39/00 | (2006.01) |

(52) U.S. Cl.
CPC ........ *C12N 15/1037* (2013.01); *C07K 14/005* (2013.01); *A61K 2039/5256* (2013.01); *A61K 2039/5258* (2013.01); *C12N 2740/16122* (2013.01); *C12N 2795/18123* (2013.01); *C40B 40/02* (2013.01)

(58) Field of Classification Search
None
See application file for complete search history.

(56) References Cited

U.S. PATENT DOCUMENTS

| 5,223,409 A | 6/1993 | Ladner et al. |
| 7,008,651 B2 | 3/2006 | Ambuel et al. |

FOREIGN PATENT DOCUMENTS

| EP | WO 2004/084940 A1 * | 10/2004 | ............. A61K 39/39 |
| WO | 2004084940 A1 | 10/2004 | |
| WO | WO 2004/084940 A1 * | 10/2004 | ............. A61K 39/39 |

OTHER PUBLICATIONS

Peabody (Jul. 15, 2003) Journal of Nanobiotechnology vol. 1 p. 1.*
Brown (Jan. 2003) Intervirology vol. 45 DOI 10.1159/000067930 pp. 371 to 380.*
Peabody (Jul. 15, 2003) Journal of Nanobiotechnology vol. 1 pp. 1 to 8.*
Short et al. (Dec. 1, 1995) Journal of Biological Chemistry vol. 270 pp. 28541 to 28550.*

(Continued)

*Primary Examiner* — Christian Boesen
(74) *Attorney, Agent, or Firm* — Henry D. Coleman; R. Neil Sudol

(57) ABSTRACT

The invention is directed to virus-like particles (VLPs) of an RNA bacteriophage that (a) comprises a coat polypeptide of said phage modified by insertion of a heterologous peptide that is displayed on said VLP and (b) encapsidates said bacteriophage mRNA as well as populations of these VLPs, and their uses. The invention is further directed to VLPs that encapsidate heterologous substances, as well as populations of these VLPs and their uses.

2 Claims, 21 Drawing Sheets

(56) References Cited

OTHER PUBLICATIONS

Ghadessy, et al. A novel emulsion mixture for in vitro compartmentalization of transcription and translation in the rabbit reticulocyte system. Protein Eng. Des. Sel. Mar. 2004 (Mar. 2004), vol. 17, No. 3, pp. 2001-2004; abstract; p. 2003, para 2.
Peabody. A Viral Platform for Chemical Modification and Multivalent Display. J. Nanobiotechnology. Jul. 15, 2003 (Jul. 15, 2003), vol. 1, No. 1, article 5, pp. 1-8.
Anderson EA et al. Viral Nanoparticles Donning a Paramagnetic Coat: Conjugation of MRI Contrast Agents to the MS2 Capsid. Nano Letters 2006, 6(6), 1160-1164.
Bachmann MF et al. The Influence of Antigen Organization on B Cell Responsiveness. Science 1993, 262, 1448-1451.
Bachmann MF et al. Neutralizing Antiviral B Cell Responses, Annual Review of Immunology 1997, 15, 235-270.
Beckett DB et al. Roles of Operator and Non-operator RNA Sequences in Bacteriophage R17 Capsid Assembly. Journal of Molecular Biology 1988, 204, 939-947.
Celts JE (editor). Cell Biology a Laboratory Handbook. 1994, vols. 1-3, Academic Press, Inc., United States of America.
Chackerian B et al. Human Immunodeficiency Virus Type 1 Coreceptors Participate in Postentry Stages in the Virus Replication Cycle and Function in Simian Immunodeficiency Virus Infection. Journal of Virology 1997, 71(5), 3932-3939.
Chackerian B et al. Induction of autoantibodies to mouse CCR5 with recombinant papillomavirus particles. Proceedings of the National Academy of Sciences USA 1999, 96, 2373-2378.
Chackerian B et al. Conjugation of a self-antigen to papillomavirus-like particles allows for efficient induction of protective autoantibodies. The Journal of Clinical Investigation 2001, 108(3), 415-423.
Chackerian B et al. Induction of Autoantibodies to CCR5 in Macaques and Subsequent Effects upon Challenge with an R5-Tropic Simian / Human Immunodeficiency Virus. Journal of Virology 2004, 78(8), 4037-4047.
Chen Z et al. Genetically Divergent Strains of Simian Immunodeficiency Virus Use CCR5 as a Coreceptor for Entry. Journal of Virology 1997, 71(4), 2705-2714.
Freshney RI (editor), Animal Cell Culture A Practical Approach Second Edition 1992 IRL Press at Oxford University Press, New York.
Gait MJ (editor), Oligonucleotide synthesis a practical approach 1984 IRL Press, Oxford, England.
Gasteiger E et al. Protein Identification and Analysis Tools on the ExPASy Server. The Proteomics Protocols Handbook 2005, J.M. Walker (ed.), pp. 571-607.
Hames BD and Higgins SJ (editors), Transcription and Translation a practical approach 1984, IRL Press Limited, Oxford, England.
Hames BD and Higgins SJ (editors), Nucleic Acid Hybridization a practical approach 1985, IRL Press Limited, Oxford, England.
Higgins SJ and Hames BD (editors), Protein Expression a practical approach 1999, Oxford University Press, Oxford England.
Higuchi R et al. A general method of in vitro preparatioon and specific mutagenesis of DNA fragments: study of protein and DNA interactions. Nucleic Acids Research 1988, 16(15) 7351-7367.
Jewett MC et al. Mimicking the *Escherichia coli* Cytoplasmic Environment Activates Long Lived and Efficient Cell-Free Protein Synthesis. Biotechnology and Bioengineering 2004, 86(1), 19-26.
Kim D-M et al. A highly efficient cell-frree protein synthesis system from *Escherichia coli*. European Journal of Biochemistry 1996, 239, 881-886.
Kimpton J et al. Detection of Replication-Competent and Pseudotyped Human Immunodeficiency Virus with a Sensitive Cell Line on the Basis of Activation of an Integrated beta-Galactosidase Gene. Journal of Virology 1992, 66(4), 2232-2239.
Kramer G et al. Cell-free coupled transcrption-translation systems from *Escherichia coli*. IN: Protein Expression. A Practical Approach, 1999, Higgins and Hames (eds.), Oxford University Press, Oxford, England.

Kyte J et al. A Simple Method for Displaying the Hydropathic Character of a Protein. Journal of Molecular Biology 1982, 157, 105-132.
Laman JD et al. Variant-Specific Monoclonal and Group-Specific Polyclonal Human Immunodeficiency Virus Type 1 Neutralizing Antibodies Raised with Synthetic Peptides from the gp120 Third Variable Domain. Journal of Virology 1992, 6(3), 1823-1831.
Lash LH. Measurement of Glutathione Transport. IN: Current Protocols in Toxicology 1999, John Wiley & Sons, Inc. (pp. 6.3.1-6.3.14).
Lehrach H et al. RNA Molecular Weight Determinations by Gel Electrophoresis under Denaturing Conditions, a Critical Reexamination. Biochemistry 1977, 116(21), 4743-4751.
Li Q et al. Overcoming antigen masking of anti-amyloidbeta antibodies reveals breaking of B cell Tolerance by virus-like particles in amyloidbeta immunized amyloid precursor protein transgenic mice. BMC Neuroscience 2004, 5, 21-27.
Mastico RA et al. Multiple presentation of foreign peptides on the surface of an RNA-free spherical bacteriophage capsid. Journal of General Virology 1993, 74, 541-548.
Maurer P et al. A therapeutic vaccine for nicotine dependence: preclinical efficacy, and phase I safety and immunogenicity. European Journal of Immunology 2005, 35, 2031-2040.
Misumi S et al. A Cyclic Dodecapeptide-Multiple-Antigen Peptide Conjugate from the Undecapeptidyl Arch (from Arg168 to Cys178) of Extracellular Loop 2 in CCR5 as a Novel Human Immunodeficiency Virus Type 1 Vaccine. Journal of Virology 2001, 75(23), 11614-11620.
Neirynck S et al. A universal influenza A vaccine based on the extracellular domain of the M2 protein. Nature Medicine 1999, 5(10), 1157-1163.
Peabody DS. Translational Repression by Bacteriophage MS2 Coat Protein Expressed from a Plasmid. The Journal of Biological Chemistry 1990, 265(10), 5684-5689.
Peabody DS. The RNA binding site of bacteriophage MS2 coat protein. The EMBO Journal 1993, 12(2), 595-600.
Peabody DS et al. Complementation of RNA binding site mutations in MS2coat protein heterodimers. Nucleic Acids Research 1996, 24(12) 2352-2359.
Peabody DS. Subunit Fusion Confers Tolerance to Peptide Insertions in a Virus Coat Protein. Archives of Biochemistry and Biophysics 1997, 347(1), 85-92.
Peabody DS et al. Asymmetric Contributions to RNA Binding by the Thr45 Residues of MS2 Coat Protein Dimer. The Journal of Biological Chemistry 1999, 274(36), 25403-25410.
Perbal B. A Practical Guide to Molecular Cloning Second Edition 1988, John Wiley & Sons, Inc., United States of America.
Powell AJ et al. Asymmetric interactions in the adenosine-binding pockets of the MS2 coat protein dimer. BMC Molecular Biology 2001, 2, 6.
Sambrook J et al. Molecular Cloning a Laboratory Manual Second Edition 1989, Cold Spring Harbor Laboratory Press, Plainview, New York, USA.
Smothers JF et al. Affinity Selection from Biological Libraries. Science 2002, 298, 621-622.
Spohn G et al. Protection against Osteoporosis by Active Immunization with TRANCE/RANKL Displayed on Virus-Like Particles. The Journal of Immunology 2005, 175, 6211-6218.
Stockley PG et al. Use of Fusions to Viral Coat Proteins as Antigenic Carriers for Vaccine Development. Methods in Enzymology 2000, 326, 551-569.
Studier FW et al. Use of T7 RNA Polymerase to Direct Expression of Cloned Genes. Methods in Enzymology 1990, 185, 60-89.
Tatusova TA et al. Blast 2 Sequences, a new tool for comparing protein and nucleotide sequences. FEMS Microbiology Letters 1999, 174, 247-250.
Tawfik DS. Man-made cell-like compartments for molecular evolution. Nature Biotechnology 1998, 16, 652-656.
Thyagarajan R et al. Polyvalent Antigens Stabilize B Cell Antigen Receptor Surface Signaling Microdomains. The Journal of Immunology 2003, 170, 6099-6106.

(56) References Cited

OTHER PUBLICATIONS

Van Houten NE et al. Phage Libraries for Developing Antibody-Targeted Diagnostics and Vaccines. IN: Phage Display in Biotechnology and Drug Discovery, 2005, Sachdev S. Sidhu (ed.),CRC Taylor & Francis Group, Boca Raton, Florida USA, pp. 165-254.
Woodward J. (editor) Immobilised cells and enzymes a practical approach 1985, IRL Press, Oxford, England.
Zubay G. In Vitro Synthesis of Protein in Microial Systems. Annual Review of Genetics 1963, 7, 267-287.

* cited by examiner

ECL2
```
  G  T    R  S  Q  R  E  G  L  H  Y  T     G  T
     T  CGCAGCCAGCGCGAAGGCTTGCATTATACC   GGTACC
CCATGA  GCGTCGGTCGCGCTTCCGAACGTAATATGG   C
```

V3
```
  G  T    I  Q  R  G  P  G  R  A  F  V     G  T
     T  ATTCAGCGCGGCCCGGGCCGCGCGTTTGTG   GGTACC
GCATGA  TAAGTCGCGCCGGGCCCGGCGCGCAAACAC   C
```

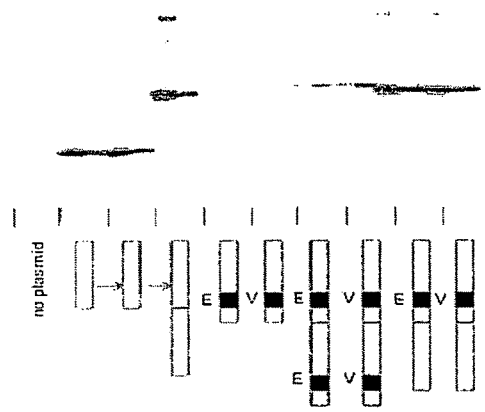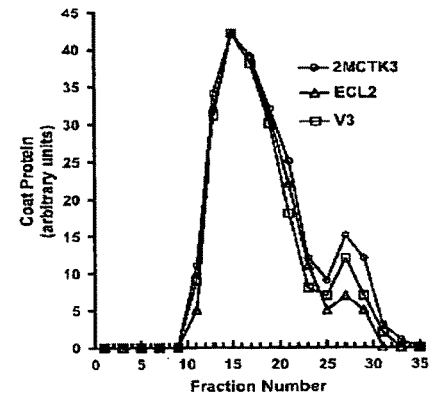
Figure 11A
Figure 11B
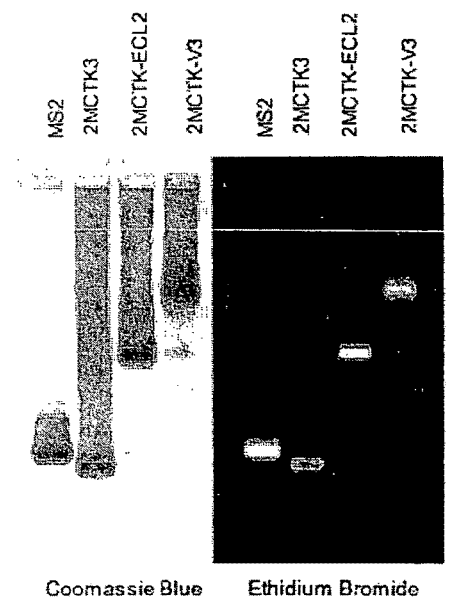
Figure 11C

SEQUENCE LISTING

```
<160> NUMBER OF SEQ ID NOS: 25

<210> SEQ ID NO 1
<211> LENGTH: 19
<212> TYPE: RNA
<213> ORGANISM: Artificial
<220> FEATURE:
<223> OTHER INFORMATION: Synthetic bacteriophage

<400> SEQUENCE: 1
acaugaggau uacccaugu                                                    19

<210> SEQ ID NO 2
<211> LENGTH: 130
<212> TYPE: PRT
<213> ORGANISM: Artificial
<220> FEATURE:
<223> OTHER INFORMATION: Synthetic peptide

<400> SEQUENCE: 2

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Trp Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 3
<211> LENGTH: 5011
<212> TYPE: DNA
<213> ORGANISM: Artificial
<220> FEATURE:
<223> OTHER INFORMATION: Synthetic bacteriophage

<400> SEQUENCE: 3
ttcttgaaga cgaaagggcc tcgtgatacg cctatttta taggttaatg tcatgataat      60
aatggtttct tagacgtcag gtggcacttt tcggggaaat gtgcgcggaa ccctatttg     120 tttattttc taaatacatt caaatatgta tccgctcatg agacaataac cctgataaat     180
gcttcaataa tattgaaaaa ggaagagtat gagtattcaa catttccgtg tcgcccttat     240 tcccttttt gcggcatttt gccttcctgt ttttgctcac ccagaaacgc tggtgaaagt     300
```

```
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacgggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct aacgtgagt tttcgttcca   1200 ctgagcgtca gaccccgtag aaaagatcaa aggatcttct tgagatcctt ttttttctgcg   1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatccctg attctgtgga   1920 taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
```

-continued

```
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360
aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gacgctctcc    3720
cttatgcgac tcctgcatta ggaagcagcc cagtagtagg ttgaggccgt tgagcaccgc    3780
cgccgcaagg aatggtgcat gcaaggagat ggcgcccaac agtcccccgg ccacggggcc    3840
tgccaccata cccacgccga acaagcgct catgagcccg aagtggcgag cccgatcttc    3900
cccatcggtg atgtcggcga tataggcgcc agcaaccgca cctgtggcgc cggtgatgcc    3960
ggccacgatg cgtccggcgt agaggatcga gatctcgatc ccgcgaaatt aatacgactc    4020
actataggga gaccacaacg gtttccctct agatagagcc ctcaaccgga gtttgaagca    4080
tggcttctaa cttttactcag ttcgttctcg tcgacaatgg cggaactggc gacgtgactg    4140
tcgccccaag caacttcgct aacggggtcg ctgaatggat cagctctaac tcgcgttcac    4200
aggcttacaa agtaacctgt agcgttcgtc agagctctgc gcagaatcgc aaatacacca    4260
tcaaagtcga ggtgcctaaa gtggcaaccc agactgttgg tggtgtagag cttcctgtag    4320
ccgcatggcg ttcgtactta aatatggaac taaccattcc aattttcgct acgaattccg    4380
actgcgagct tattgttaag gcaatgcaag gtctcctaaa agatggaaac ccgattccct    4440
cagcaatcgc agcaaactcc ggcatctact aatagacgcc ggggttaatt aattaaggat    4500
ccggctgcta acaaagcccg aaaggaagct gagttggctg ctgccaccgc tgagcaataa    4560
ctagcataac cccttggggc ctctaaacgg gtcttgaggg gttttttgct gaaaggagga    4620
actatatccg gatatccaca ggacgggtgt ggtcgccatg atcgcgtagt cgatagtggc    4680
tccaagtagc gaagcgagca ggactgggcg gcggccaaag cggtcggaca gtgctccgag    4740
aacgggtgcg catagaaatt gcatcaacgc atatagcgct agcagcacgc catagtgact    4800
ggcgatgctg tcggaatgga cgatatcccg caagaggccc ggcagtaccg gcataaccaa    4860
gcctatgcct acagcatcca gggtgacggt gccgaggatg acgatgagcg cattgttaga    4920
tttcatacac ggtgcctgac tgcgttagca atttaactgt gataaactac cgcattaaag    4980
cttatcgatg ataagctgtc aaacatgaga a                                   5011
```

-continued

```
<210> SEQ ID NO 4
<211> LENGTH: 14
<212> TYPE: PRT
<213> ORGANISM: Artificial
<220> FEATURE:
<223> OTHER INFORMATION: Synthetic peptide

<400> SEQUENCE: 4

Gly Thr Arg Ser Gln Arg Glu Gly Leu His Tyr Thr Gly Thr
1               5                   10

<210> SEQ ID NO 5
<211> LENGTH: 37
<212> TYPE: DNA
<213> ORGANISM: Artificial
<220> FEATURE:
<223> OTHER INFORMATION: Annealed oligonucleotide

<400> SEQUENCE: 5
tcgcagccag cgcgaaggct tgcattatac cggtacc                              37

<210> SEQ ID NO 6
<211> LENGTH: 37
<212> TYPE: DNA
<213> ORGANISM: Artificial
<220> FEATURE:
<223> OTHER INFORMATION: Annealed oligonucleotide

<400> SEQUENCE: 6
ccatgagcgt cggtcgcgct tccgaacgta atatggc                              37

<210> SEQ ID NO 7
<211> LENGTH: 14
<212> TYPE: PRT
<213> ORGANISM: Artificial
<220> FEATURE:
<223> OTHER INFORMATION: Synthetic peptide

<400> SEQUENCE: 7

Gly Thr Ile Gln Arg Gly Pro Gly Arg Ala Phe Val Gly Thr
1               5                   10

<210> SEQ ID NO 8
<211> LENGTH: 37
<212> TYPE: DNA
<213> ORGANISM: Artificial
<220> FEATURE:
<223> OTHER INFORMATION: Annealed oligonucleotide

<400> SEQUENCE: 8
tattcagcgc ggcccgggcc gcgcgtttgt gggtacc                              37

<210> SEQ ID NO 9
<211> LENGTH: 37
<212> TYPE: DNA
<213> ORGANISM: Artificial
<220> FEATURE:
<223> OTHER INFORMATION: Annealed oligonucleotide

<400> SEQUENCE: 9
gcatgataag tcgcgccggg cccggcgcgc aaacacc                              37

<210> SEQ ID NO 10
<211> LENGTH: 30
<212> TYPE: DNA
<213> ORGANISM: Artificial
```

```
<220> FEATURE:
<223> OTHER INFORMATION: Synthetic nucleotide

<400> SEQUENCE: 10
cgagttagag ctgatccatt cagcgacccc                                          30

<210> SEQ ID NO 11
<211> LENGTH: 14
<212> TYPE: PRT
<213> ORGANISM: Artificial
<220> FEATURE:
<223> OTHER INFORMATION: Synthetic peptide

<400> SEQUENCE: 11

Arg Ile Gln Arg Gly Pro Gly Arg Ala Phe Val Thr Gly Lys
1               5                   10

<210> SEQ ID NO 12
<211> LENGTH: 258
<212> TYPE: PRT
<213> ORGANISM: Artificial
<220> FEATURE:
<223> OTHER INFORMATION: Synthetic peptide

<400> SEQUENCE: 12
```

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
        50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Trp Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Gly Asn Phe Thr Gln Phe Val Leu Val Asp Asn Gly Gly Thr
    130                 135                 140

Gly Asp Val Thr Val Ala Pro Ser Asn Phe Ala Asn Gly Val Ala Glu
145                 150                 155                 160

Trp Ile Ser Ser Asn Ser Arg Ser Gln Ala Tyr Lys Val Thr Cys Ser
                165                 170                 175

Val Arg Gln Ser Ser Ala Gln Asn Arg Lys Tyr Thr Ile Lys Val Glu
            180                 185                 190

Val Pro Lys Val Ala Thr Gln Thr Val Gly Gly Val Glu Leu Pro Val
        195                 200                 205

Ala Ala Trp Arg Ser Tyr Leu Asn Met Glu Leu Thr Ile Pro Ile Phe
    210                 215                 220

Ala Thr Asn Trp Asp Cys Glu Leu Ile Val Lys Ala Met Gln Gly Leu
225                 230                 235                 240

Leu Lys Asp Gly Asn Pro Ile Pro Ser Ala Ile Ala Ala Asn Ser Gly
                245                 250                 255

Ile Tyr

<210> SEQ ID NO 13
<211> LENGTH: 20
<212> TYPE: DNA
<213> ORGANISM: Artificial
<220> FEATURE:
<223> OTHER INFORMATION: Synthetic oligonucleotide

<400> SEQUENCE: 13
gttgtaaaac gacggccagt                                               20

<210> SEQ ID NO 14
<211> LENGTH: 60
<212> TYPE: DNA
<213> ORGANISM: Artificial
<220> FEATURE:
<223> OTHER INFORMATION: Synthetic oligoneucleotide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 14
cgcggtaccn nsnnsnnsnn snnsnnsnns nnsnnsnnsg aactggcga cgtgactgtc    60

<210> SEQ ID NO 15
<211> LENGTH: 61
<212> TYPE: DNA
<213> ORGANISM: Artificial
<220> FEATURE:
<223> OTHER INFORMATION: Synthetic oligoneucleotide
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

```
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 15
ccccgtcgac aatggcnnsn nsnnsnnsnn snnsnnsnns ggaactggcg acgtgactgt     60
c                                                                    61

<210> SEQ ID NO 16
<211> LENGTH: 60
<212> TYPE: DNA
<213> ORGANISM: Artificial
<220> FEATURE:
<223> OTHER INFORMATION: Synthetic oligoneucleotide
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 16
ccccgtcgac aatggcnnsn nsnnsnnsnn snnsnnsnng gcgacgtgac tgtcgcccca     60
```

<210> SEQ ID NO 17
<211> LENGTH: 58
<212> TYPE: DNA
<213> ORGANISM: Artificial
<220> FEATURE:
<223> OTHER INFORMATION: Synthetic oligoneucleotide
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 17
ccccgtcgac aatnnsnnsn nsnnsnnsnn snnsnnsgac gtgactgtcg ccccaagc        58

<210> SEQ ID NO 18
<211> LENGTH: 5395
<212> TYPE: DNA
<213> ORGANISM: Artificial
<220> FEATURE:
<223> OTHER INFORMATION: Synthetic nucleotide

<400> SEQUENCE: 18
ttcttgaaga cgaaagggcc tcgtgatacg cctatttttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtat gagtattcaa catttccgtg tcgcccttat     240
tccctttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg ctttttttgca     660 caacatgggg gatcatgtaa ctcgccttga tcgttgggaa ccggagctga atgaagccat     720
accaaacgac gagcgtgaca ccacgatgcc tgcagcaatg gcaacaacgt tgcgcaaact     780

```
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct aacgtgagt tttcgttcca    1200 ctgagcgtca gacccgtag aaaagatcaa aggatcttct tgagatcctt ttttctgcg    1260 cgtaatctgc tgcttgcaaa caaaaaaacc accgctacca gcggtggttt gtttgccgga   1320
tcaagagcta ccaactctt ttccgaaggt aactggcttc agcagagcgc agataccaaa    1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca gaccaacg ctgcccgaga    2940 tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
```

-continued

| | |
|---|---|
| ccatgtgctc gccgaggcgg cataaatcgc cgtgacgatc agcggtccag tgatcgaagt | 3240 |
| taggctggta agagccgcga gcgatccttg aagctgtccc tgatggtcgt catctacctg | 3300 |
| cctggacagc atggcctgca acgcgggcat cccgatgccg ccggaagcga aagaatcat | 3360 |
| aatggggaag gccatccagc ctcgcgtcgc gaacgccagc aagacgtagc ccagcgcgtc | 3420 |
| ggccgccatg ccggcgataa tggcctgctt ctcgccgaaa cgtttggtgg cgggaccagt | 3480 |
| gacgaaggct tgagcgaggg cgtgcaagat tccgaatacc gcaagcgaca ggccgatcat | 3540 |
| cgtcgcgctc agcgaaagc ggtcctcgcc gaaaatgacc cagagcgctg ccggcacctg | 3600 |
| tcctacgagt tgcatgataa agaagacagt cataagtgcg cgacgatag tcatgccccg | 3660 |
| cgcccaccgg aaggagctga ctggggttgaa ggctctcaag ggcatcggtc gacgctctcc | 3720 |
| cttatgcgac tcctgcatta ggaagcagcc cagtagtagg ttgaggccgt tgagcaccgc | 3780 |
| cgccgcaagg aatggtgcat gcaaggagat ggcgcccaac agtcccccgg ccacggggcc | 3840 |
| tgccaccata cccacgccga aacaagcgct catgagcccg aagtggcgag cccgatcttc | 3900 |
| cccatcggtg atgtcggcga tataggcgcc agcaaccgca cctgtggcgc cggtgatgcc | 3960 |
| ggccacgatg cgtccggcgt agaggatcga gatctcgatc ccgcgaaatt aatacgactc | 4020 |
| actataggga gaccacaacg gtttccctct agatagagc ctcaaccgga gtttgaagca | 4080 |
| tggcttctaa ctttactcag ttcgttctcg tcgacaatgg cggaactggc gacgtgactg | 4140 |
| tcgccccaag caacttcgct aacggggtcg ctgaatggat cagctctaac tcgcgttcac | 4200 |
| aggcttacaa agtaacctgt agcgttcgtc agagctctgc gcagaatcgc aaatacacca | 4260 |
| tcaaagtcga ggtgcctaaa gtggcaaccc agactgttgg tggtgtagag cttcctgtag | 4320 |
| ccgcatggcg ttcgtactta aatatggaac taaccattcc aattttcgct acgaattccg | 4380 |
| actgcgagct tattgttaag gcaatgcaag gtctcctaaa agatggaaac ccgattccct | 4440 |
| cagcaatcgc agcaaactcc ggcctctacg gcaactttac tcagttcgtt ctcgtcgaca | 4500 |
| atggcggtac cggcgacgtg actgtcgccc caagcaactt cgctaacggg gtcgctgaat | 4560 |
| ggatcagctc taactcgcgt tcacaggctt acaaagtaac ctgtagcgtt cgtcagagct | 4620 |
| ctgcgcagaa tcgcaaatac accatcaaag tcgaggtgcc taaagtggca acccagactg | 4680 |
| ttggtggtgt agagcttcct gtagccgcat ggcgttcgta cttaaatatg gaactaacca | 4740 |
| ttccaatttt cgctacgaat tccgactgcg agcttattgt taaggcaatg caaggtctcc | 4800 |
| taaaagatgg aaacccgatt ccctcagcaa tcgcagcaaa ctccggcatc tactaataga | 4860 |
| cgccgggtta attaattaag gatcccggct gctaacaaag cccgaaagga agctgagttg | 4920 |
| gctgctgcca ccgctgagca ataactagca taacccttg gggcctctaa acgggtcttg | 4980 |
| aggggttttt tgctgaaagg aggaactata tccggatatc cacaggacgg gtgtggtcgc | 5040 |
| catgatcgcg tagtcgatag tggctccaag tagcgaagcg agcaggactg ggcggcggcc | 5100 |
| aaagcggtcg acagtgctc cgagaacggg tgcgcataga aattgcatca acgcatatag | 5160 |
| cgctagcagc acgccatagt gactggcgat gctgtcggaa tggacgatat cccgcaagag | 5220 |
| gcccggcagt accggcataa ccaagcctat gcctacagca tccagggtga cggtgccgag | 5280 |
| gatgacgatg agcgcattgt tagatttcat acacggtgcc tgactgcgtt agcaatttaa | 5340 |
| ctgtgataaa ctaccgcatt aaagcttatc gatgataagc tgtcaaacat gagaa | 5395 |

<210> SEQ ID NO 19
<211> LENGTH: 3587
<212> TYPE: DNA
<213> ORGANISM: Artificial
<220> FEATURE:
<223> OTHER INFORMATION: Synthetic polynucleotide

<400> SEQUENCE: 19

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttaatt taaaaggatc taggtgaaga    1140
tcctttttga taatctcatg accaaaatcc cttaacgtga gttttcgttc cactgagcgt    1200
cagaccccgt agaaaagatc aaaggatctt cttgagatcc tttttttctg cgcgtaatct    1260
gctgcttgca acaaaaaaa ccaccgctac cagcggtggt ttgtttgccg gatcaagagc    1320
taccaactct ttttccgaag gtaactggct tcagcagagc gcagatacca atactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttttgtga tgctcgtcag    1800
gggggcggag cctatggaaa aacgccagca acgcggcctt tttacggttc ctggccttt    1860
gctggccttt tgctcacatg ttctttcctg cgttatcccc tgattctgtg ataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
```

```
accatgatta cgccaagctt gcatgcctgc aggtcgactc tagatagagc cctcaaccgg    2280
agtttgaacc atggcttcta actttactca gttcgttctc gtcgacaatg gcggaactgg    2340
cgacgtgact gtcgccccaa gcaacttcgc taacgggtc gctgaatgga tcagctctaa     2400
ctcgcgttca caggcttaca aagtaacctg tagcgttcgt cagagctctg cgcagaatcg    2460
caaatacacc atcaaagtcg aggtgcctaa agtggcaacc cagactgttg gtggtgtaga    2520
gcttcctgta gccgcatggc gttcgtactt aaatatggaa ctaaccattc caattttcgc    2580
tacgaattcc gactgcgagc ttattgttaa ggcaatgcaa ggtctcctaa aagatggaaa    2640
cccgattccc tcagcaatcg cagcaaactc cggcatctac taatagacgc cgggttaatt    2700
aattaaggat ccaattcact ggccgtcgtt ttacaacgtc gtgactggga aaaccctggc    2760
gttacccaac ttaatcgcct tgcagcacat ccccctttcg ccatctggcg taatagcgaa    2820
gaggcccgca ccgatcgccc ttcccaacag ttgcgcagcc tgaatggcga atggcgcctg    2880
atgcggtatt ttctccttac gcatctgtgc ggtatttcac accgcatacg tcaaagcaac    2940
catagtacgc gccctgtagc ggcgcattaa gcgcggcggg tgtggtggtt acgcgcagcg    3000
tgaccgctac acttgccagc gccctagcgc ccgctccttt cgctttcttc ccttcctttc    3060
tcgccacgtt cgccggcttt ccccgtcaag ctctaaatcg gggctccct ttagggttcc      3120 gatttagtgc tttacggcac ctcgacccca aaaacttgat ttgggtgatg gttcacgtag    3180
tgggccatcg ccctgataga cggttttcg ccctttgacg ttggagtcca cgttctttaa     3240
tagtggactc ttgttccaaa ctggaacaac actcaaccct atctcgggct attcttttga    3300
tttataaggg attttgccga tttcggccta ttggttaaaa aatgagctga tttaacaaaa    3360
atttaacgcg aattttaaca aaatattaac gtttacaatt ttatggtgca ctctcagtac    3420
aatctgctct gatgccgcat agttaagcca gccccgacac ccgccaacac ccgctgacgc    3480
gccctgacgg gcttgtctgc tcccggcatc cgcttacaga caagctgtga ccgtctccgg    3540
gagctgcatg tgtcagaggt tttcaccgtc atcaccgaaa cgcgcga               3587
```

<210> SEQ ID NO 20
<211> LENGTH: 3621
<212> TYPE: DNA
<213> ORGANISM: Artificial
<220> FEATURE:
<223> OTHER INFORMATION: Synthetic polynucleotide

<400> SEQUENCE: 20

```
gacgaaaggg cctcgtgata cgcctatttt tataggttaa tgtcatgata ataatggttt      60
cttagacgtc aggtggcact tttcggggaa atgtgcgcgg aaccctatt tgtttatttt       120 tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttgctc acccagaaac gctggtgaaa gtaaaagatg       300
ctgaagatca gttgggtgca cgagtgggt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
```

```
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttttt   1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gcatgcctgc aggtcgactc tagatagagc cctcaaccgg   2280
agtttgaagc atggcttcta actttactca gttcgttctc gtcgacaatg gcggtaccgg   2340
cgacgtgact gtcgccccaa gcaacttcgc taacggggtc gctgaatgga tcagctctaa   2400
ctcgcgttca caggcttaca aagtaacctg tagcgttcgt cagagctctg cgcagaatcg   2460
caaatacacc atcaaagtcg aggtgcctaa agtggcaacc cagactgttg gtggtgtaga   2520
gcttcctgta gccgcatggc gttcgtactt aaatatggaa ctaaccattc caattttcgc   2580
tacgaattcc gactgcgagc ttattgttaa ggcaatgcaa ggtctcctaa aagatggaaa   2640
cccgattccc tcagcaatcg cagcaaactc cggcatctac taatagacgc cggccattca   2700
aacatgagga ttacccatgt cgaagacaac aaagaagttc ggatccaatt cactggccgt   2760
cgttttacaa cgtcgtgact gggaaaaccc tggcgttacc caacttaatc gccttgcagc   2820
acatccccct ttcgccatct ggcgtaatag cgaagaggcc cgcaccgatc gcccttccca   2880
acagttgcgc agcctgaatg gcgaatggcg cctgatgcgg tattttctcc ttacgcatct   2940
gtgcggtatt tcacaccgca tacgtcaaag caaccatagt acgcgccctg tagcggcgca   3000
ttaagcgcgg cgggtgtggt ggttacgcgc agcgtgaccg ctacacttgc cagcgcccta   3060
gcgcccgctc ctttcgcttt cttcccttcc tttctcgcca cgttcgccgg ctttccccgt   3120
```

```
caagctctaa atcgggggct ccctttaggg ttccgattta gtgctttacg gcacctcgac    3180
cccaaaaact tgatttgggt gatggttcac gtagtgggcc atcgccctga tagacggttt    3240
ttcgcccttt gacgttggag tccacgttct ttaatagtgg actcttgttc caaactggaa    3300
caacactcaa ccctatctcg ggctattctt ttgatttata agggattttg ccgatttcgg    3360
cctattggtt aaaaaatgag ctgatttaac aaaaatttaa cgcgaatttt aacaaaatat    3420
taacgtttac aattttatgg tgcactctca gtacaatctg ctctgatgcc gcatagttaa    3480
gccagccccg acaccgccca caccgctg acgcgccctg acgggcttgt ctgctcccgg     3540
catccgctta cagacaagct gtgaccgtct ccgggagctg catgtgtcag aggttttcac    3600
cgtcatcacc gaaacgcgcg a                                              3621
```

<210> SEQ ID NO 21
<211> LENGTH: 5394
<212> TYPE: DNA
<213> ORGANISM: Artificial
<220> FEATURE:
<223> OTHER INFORMATION: Synthetic polynucleotide

<400> SEQUENCE: 21

```
ttcttgaaga cgaaagggcc tcgtgatacg cctatttta taggttaatg tcatgataat      60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240 tcccttttt gcggcatttt gccttcctgt ttttgctcac ccagaaacgc tggtgaaagt     300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt ttttttctgcg   1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
```

-continued

```
gggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttt tacggttcct    1860
ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg tcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460
tgtaagggg atttctgttc atggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggaccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360
aatgggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag gcatcggtc gacgctctcc    3720
cttatgcgac tcctgcatta ggaagcagcc cagtagtagg ttgaggccgt tgagcaccgc    3780
cgccgcaagg aatggtgcat gcaaggagat ggcgcccaac agtccccgg ccacggggcc    3840
tgccaccata cccacgccga aacaagcgct catgagcccg aagtggcgag cccgatcttc    3900
cccatcggtg atgtcggcga tataggcgcc agcaaccgca cctgtggcgc cggtgatgcc    3960
```

| | | | | |
|---|---|---|---|---|
| ggccacgatg | cgtccggcgt | agaggatcga | gatctcgatc | ccgcgaaatt aatacgactc | 4020 |
| actataggga | gaccacaacg | gtttccctct | agatagagcc | ctcaaccgga gtttgaagca | 4080 |
| tggcttctaa | ctttactcag | ttcgttctcg | tcgacaatgg | cggaactggc gacgtgactg | 4140 |
| tcgcccaag | caacttcgct | aacggggtcg | ctgaatggat | cagctctaac tcgcgttcac | 4200 |
| aggcttacaa | agtaacctgt | agcgttcgtc | agagctctgc | gcagaatcgc aaatacacca | 4260 |
| tcaaagtcga | ggtgcctaaa | gtggcaaccc | agactgttgg | tggtgtagag cttcctgtag | 4320 |
| ccgcatggcg | ttcgtactta | aatatggaac | taaccattcc | aattttcgct acgaattccg | 4380 |
| actgcgagct | tattgttaag | gcaatgcaag | gtctcctaaa | agatggaaac ccgattccct | 4440 |
| cagcaatcgc | agcaaactcc | ggcatctacg | ctaactttac | tcagttcgtt ctcgtcgaca | 4500 |
| atggcggaac | tggcgacgtg | actgtcgccc | aagcaacctt | cgctaacggg gtcgctgaat | 4560 |
| ggatcagctc | taactcgcgt | tcacaggctt | acaaagtaac | ctgtagcgtt cgtcagagct | 4620 |
| ctgcgcagaa | tcgcaaatac | accatcaaag | tcgaggtgcc | taaagtggca acccagactg | 4680 |
| ttggtggtgt | agagcttcct | gtagccgcat | ggcgttcgta | cttaaatatg gaactaacca | 4740 |
| ttccaatttt | cgctacgaat | tccgactgcg | agcttattgt | taaggcaatg caaggtctcc | 4800 |
| taaaagatgg | aaacccgatt | ccctcagcaa | tcgcagcaaa | ctccggcatc tactaataga | 4860 |
| cgccgggtta | attaattaag | gatccggctg | ctaacaaagc | ccgaaaggaa gctgagttgg | 4920 |
| ctgctgccac | cgctgagcaa | taactagcat | aaccccttgg | ggcctctaaa cgggtcttga | 4980 |
| ggggtttttt | gctgaaagga | ggaactatat | ccggatatcc | acaggacggg tgtggtcgcc | 5040 |
| atgatcgcgt | agtcgatagt | ggctccaagt | agcgaagcga | gcaggactgg gcggcggcca | 5100 |
| aagcggtcgg | acagtgctcc | gagaacgggt | gcgcatagaa | attgcatcaa cgcatatagc | 5160 |
| gctagcagca | cgccatagtg | actggcgatg | ctgtcggaat | ggacgatatc ccgcaagagg | 5220 |
| cccggcagta | ccggcataac | caagcctatg | cctacagcat | ccagggtgac ggtgccgagg | 5280 |
| atgacgatga | gcgcattgtt | agatttcata | cacggtgcct | gactgcgtta gcaatttaac | 5340 |
| tgtgataaac | taccgcatta | agcttatcg | atgataagct | gtcaaacatg agaa | 5394 |

```
<210> SEQ ID NO 22
<211> LENGTH: 18
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
```

<400> SEQUENCE: 22
nnynnynnyn nynnynny                                                          18

<210> SEQ ID NO 23
<211> LENGTH: 24
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 23
nnynnynnyn nynnynnynn ynny                                                   24

<210> SEQ ID NO 24
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

```
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 24
nnynnynnyn nynnynnynn ynnynnynny                            30

<210> SEQ ID NO 25
<211> LENGTH: 12
<212> TYPE: PRT
<213> ORGANISM: Artificial
<220> FEATURE:
<223> OTHER INFORMATION: CCR5 ECL2

<400> SEQUENCE: 25

Cys Asp Arg Ser Gln Arg Glu Leu His Tyr Thr Gly
1               5                   10
```

VIRUS-LIKE PLATFORM FOR RAPID VACCINE DISCOVERY

PRIORITY CLAIM

This application claims priority from application Ser. No. 60/839,619, filed Aug. 23, 2006 and application Ser. No. 60/899,237, filed Feb. 2, 2007, the contents of which are incorporated herein by reference.

GOVERNMENT INTEREST

This patent application was supported by grant NOS. R01 GM042901 and R01 AI065240 from the National Institutes of Health. The Government has certain rights in the invention.

FIELD OF THE INVENTION

The invention is directed to virus-like particles (VLPs) of an RNA bacteriophage that (a) comprises a coat polypeptide of said phage modified by insertion of a heterologous peptide and said heterologous peptide is displayed on said VLP and (b) encapsidates said bacteriophage mRNA. The invention is also directed to a population of these VLPs and a composition comprising one or more of these VLPs and methods for obtaining these VLPs. Furthermore, the invention is directed to uses of these VLPs in identifying peptides of interest.

BACKGROUND OF THE INVENTION

The growth of recombinant DNA technology in recent years has led to the introduction of vaccines in which an immunogenic protein has been identified, cloned and expressed in a suitable host to obtain sufficient quantities of protein to allow effective protective immunization in both animals and humans. Many of the most effective vaccines are based on the potent ability of virion surfaces to elicit neutralizing antibodies. These include licensed killed or attenuated virus vaccines, such as polio, influenza and rabies, which effectively induce protective antibody responses. More recently, subunit vaccines based upon self-assemblages of the structural proteins of human papillomavirus (HPV) and hepatitis B virus (HBV) have been approved by the Food and Drug Administration.

Phage display is one of several technologies that make possible the presentation of large libraries of random amino acid sequences with the purpose of selecting from them peptides with certain specific functions. The basic idea is to create recombinant bacteriophage genomes containing a library of randomized sequences genetically fused to one of the structural proteins of the virion. When such recombinants are transfected into bacteria each produces virus particles that display a particular peptide on their surface and which package the same recombinant genome that encodes that peptide, thus establishing the linkage of genotype and phenotype essential to the method. Arbitrary functions (e.g. the binding of a receptor, immunogenicity) can be selected from such libraries by the use of biopanning and other techniques. Because of constraints imposed by the need to transform and subsequently cultivate bacteria, the practical upper limit on peptide library complexity in phage display is said to be around $10^{10}$-$10^{11}$ [Smothers et al., 2002, *Science* 298:621-622]. This requirement for passage through *E. coli* is the result of the relatively complex makeup of the virions of the phages used for phage display, and the consequent necessity that their components be synthesized and assembled in vivo. For example, display of certain peptides is restricted when filamentous phage is used, or not possible, since the fused peptide has to be secreted through the *E. coli* membranes as part of the phage assembly apparatus.

SUMMARY OF THE INVENTION

The invention is directed to a population or library of virus-like particles (VLPs), wherein each particle (a) is a VLP of an RNA bacteriophage, (b) comprises a coat polypeptide of said bacteriophage modified by insertion of a heterologous peptide wherein said heterologous peptide is displayed on said bacteriophage and (c) encapsidates said bacteriophage mRNA. In a particular embodiment, the VLPs are VLPs of an MS2 RNA bacteriophage and/or the coat polypeptide is a single chain dimer containing an upstream or downstream subunit where optionally the heterologous peptide is inserted either in the upstream or preferably downstream subunit or alternatively, the N-terminus or C-terminus of the coat polypeptide. In a particular embodiment, the heterologous peptide is at least four amino acid sequences in length. In yet another particular embodiment, at least 90 copies of said heterologous peptide is displayed on said VLP; in yet a further embodiment, between 1-180 copies of said heterologous peptide is displayed on said VLP.

The population or library of VLP particles of the present invention may be obtained by providing a plurality of transcription units comprising a bacterial or bacteriophage promoter, a coding sequence of an RNA bacteriophage single chain coat polypeptide dimer with a site for insertion of a heterologous peptide in the downstream or upstream subunit of the dimer and bacterial or bacteriophage terminator; (b) treating said transcription units of (a) with a restriction enzyme; (c) inserting coding sequences for heterologous peptides into said transcription units to obtain a population of transcription units; (d) expressing said transcription units of (c) and (e) isolating said library. In a specific embodiment, the invention comprises: (a) providing a transcription unit comprising a bacteriophage promoter, a coding sequence for a modified RNA bacteriophage coat polypeptide, wherein said modification is a heterologous peptide sequence, optionally at least 4 amino acid sequences in length, and optionally a bacteriophage terminator; (b) expressing said transcription unit in a coupled transcription/translation system from a nucleic acid template optionally in a compartmentalized water/oil emulsion and (c) recovering said population from said transcription/translation system.

The invention is further directed to the isolated transcription units mentioned above. In a specific embodiment, the transcription unit comprises a bacterial or bacteriophage promoter, a coding sequence of an RNA bacteriophage single chain coat polypeptide with a site for insertion of a heterologous peptide in said coding sequence and optionally bacteriophage terminator. In a more specific embodiment, the coat polypeptide is a single chain coat polypeptide dimer with an upstream subunit and downstream subunit with a site for insertion of a heterologous peptide in either the upstream or downstream subunit of the dimer. In a particular embodiment, the heterologous peptide is inserted in the downstream subunit. In yet another embodiment, the transcription unit is free of translational operator sequence (also referred to herein as coat recognition site, packaging signal, RNA binding site, translational operator signal).

Additionally, the population of the present invention may be used to identifying a peptide having a property of interest.

This method comprises: (a) providing the population or library of the present invention and (b) assaying heterologous peptides expressed on the VLPs in the population of the present invention for the property of interest to identify the peptide of interest. The property of interest may be immunogenicity (e.g., ability to act as an eptiope or mimitope), pharmacological effectiveness, ability to bind to filamentous phage, ability to bind to a cell surface receptor.

In a related aspect, the invention is directed to a method for isolating an immunogenic protein comprising (a) identifying said immunogenic peptide from a population of VLPs according to the method of the present invention; (b) amplifying said identified immunogenic peptide and (c) isolating said immunogenic peptide. In a particular embodiment, the immunogenic peptide is an immunogenic fragment of a self-antigen. Alternatively, the immunogenic peptide, the immunogenic peptide is a fragment of an immunogenic HIV peptide.

The invention is also directed to an isolated VLP of an RNA bacteriophage which comprises a single-chain dimer of coat polypeptide of said phage modified by insertion of a heterologous peptide, optionally at least 4 amino acids in length, wherein said heterologous peptide is displayed on said VLP, wherein said heterologous peptide is selected from the group consisting of an HIV peptide, a self antigen, a receptor and a ligand which binds to a cell surface receptor, a peptide with affinity for either end of a filamentous phage particle specific peptide, metal binding peptide, a peptide with affinity for said bacteriophage surface and/or promotes self-assembly. In a related aspect, the invention is directed to a composition comprising one or more of said isolated VLPs. In one particular embodiment, the VLP comprises a modified coat polypeptide comprising a pharmaceutically effective heterologous polypeptide coupled to a ligand for binding to a cell receptor. In another related aspect, the VLPs coupled to a detectable label (e.g., metal chelator, biotin). In another related aspect, the invention is directed to a composition comprising one or more of the VLPs of the present invention.

In a more specific embodiment, the invention is directed to an immunogenic composition comprising one or more VLPs of a MS2 RNA bacteriophage and comprises a single chain dimer of the coat polypeptide of said phage, said coat polypeptide comprising an upstream and downstream subunit, wherein said upstream or downstream subunit is modified by insertion of an immunogenic heterologous peptide in either the upstream or downstream subunit of said dimer. The immunogenic composition may be a vaccine.

BRIEF DESCRIPTION OF THE FIGURES

FIG. 11(A) Western blot analysis of the proteins produced by the various constructs described in the text and illustrated schematically here. In each case, a cell lysate was produced by sonication and then segregated into soluble (S) and insoluble (or pellet, P) fractions by centrifugation. Coat proteins were visualized using rabbit anti-MS2 serum and an alkaline phosphatase-labeled second antibody. FIG. 11(B) show elution of coat proteins from Sepharose CL-4B. Cell extracts were applied to the column and the coat protein content of individual fractions was determined by SDS-polyacrylamide gel electrophoresis. Proteins were visualized in the gel both by Coomassie Blue staining and by Western Blot, and the quantity of coat in each fraction was determined by densitometry. Authentic MS2 virus co-elutes with the VLPs produced by the recombinants. FIG. 11(C) shows agarose gel electrophoresis of purified bacteriophage MS2 and the VLPs produced by the single-chain dimer construct and by the ECL2 and V3 recombinant VLPs. Protein was stained with Coomassie Blue R250 (left). Because the VLPs contain RNA they can also be visualized with ethidium bromide (at right).

FIG. 12(A) shows an anti-V3 mAb binds to V3-VLPs, but not ECL2-VLPs or wild-type MS2 VLPs. Dilutions of MAbIIIB-V3-13 were reacted with 500 ng/well of V3-VLPs (v), wild-type MS2 VLPs (o), or ECL2-VLPs(λ). Binding was detected using a horseradish peroxidase-labeled goat anti-mouse IgG secondary followed by development with ABTS. Reactivity was measured by optical density at 405 nm ($OD_{405}$). FIG. 12 (C) Neutralization of HIV-$1_{LAI}$ infection of the MAGI-CCR5 indicator cell line using sera from mice immunized with V3-VLPs. Approximately 100 infectious virus particles were incubated with dilutions of pooled sera from mice immunized with wild-type MS2 VLPs, pooled sera from mice immunized with V3-VLPs, or the HIV neutralizing mAbs 3-13 or b12 (a potent neutralizing monoclonal antibody that recognizes an epitope outside of the V3 domain) for 1 h and then added to target cells. Two days after infection, infected cells were scored by counting the number of blue cells in each well. Inhibition of HIV infection was determined by comparing the number of blue (infected) nuclei in the presence of antibody versus the number of blue nuclei in the absence of antibody. Data represents the average of two different experiments; error bars show standard error of the mean. FIG. 12(D) Flow cytometric analysis of antibody binding to transiently transfected 293T cells. Cells were mock-transfected (shaded histogram) or transfected with pc.Rh-CCR5 (thick solid line) and then incubated with (upper left) a PE-labeled anti-CCR5 mAb (3A9), (upper right) secondary antibody alone, (lower left) sera from a mouse immunized with wild-type MS2 VLPs, or (lower right) sera from a mouse immunized with ECL2-VLPs.

DETAILED DESCRIPTION OF THE INVENTION

Figures 1A, 1B:
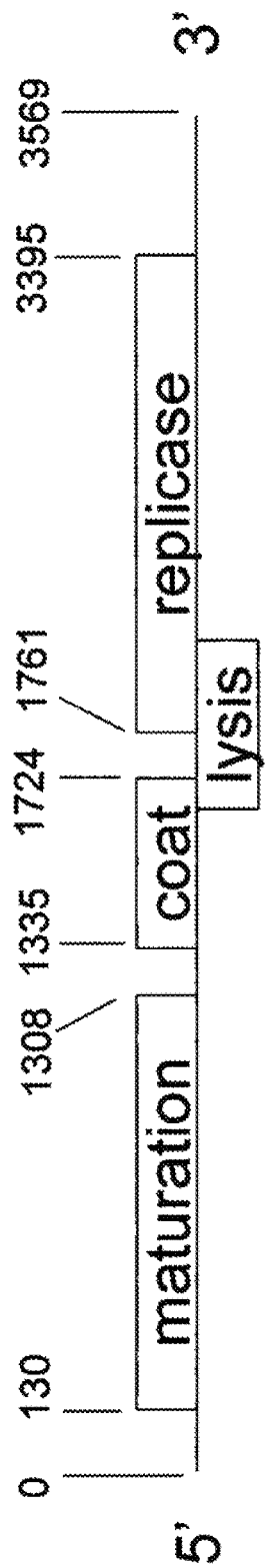
FIG. 1A shows a schematic representation of the 3569-nucleotide genome of RNA bacteriophage MS2.
FIG. 1B shows the sequence of the translational operator (SEQ ID NO:1).

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "origin of replication" refers to those DNA sequences that participate in DNA synthesis.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8-10 such amino acids. Methods of determining the spatial conformation of amino acids are known in the art, and include, for example, x-ray crystallography and 2-dimensional nuclear magnetic resonance.

As used herein, a "mimitope", is a peptide that mimics an authentic antigenic epitope.

As used herein, the term "coat protein(s)" refers to the protein(s) of a bacteriophage or a RNA-phage capable of being incorporated within the capsid assembly of the bacteriophage or the RNA-phage.

As used herein, a "coat polypeptide" as defined herein is a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

As used herein, the term "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self.

As used herein, the term "vaccine" refers to a formulation which contains the composition of the present invention and which is in a form that is capable of being administered to an animal.

As used herein, the term "virus-like particle of a bacteriophage" refers to a virus-like particle (VLP) resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host.

This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA bacteriophage coat protein: The capsid structure formed from the self-assembly of between 1-180 subunits of RNA bacteriophage coat protein and optionally containing host RNA is referred to as a "VLP of RNA bacteriophage coat protein".

A nucleic acid molecule is "operatively linked" to an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.×SSC, 0.1% SDS at 50° C., preferably at 55° C., and more preferably at 60° C. or 65° C.

Production of Virus-Like Particles

The present invention is directed to virus-like phage particles as well as methods for producing these particles in vitro. The resulting phage can be used to conduct phage display in vitro The invention makes it possible to increase laboratory complexity and reduce the time needed for iterative selection. The methods typically include producing virions in vitro and recovering the virions. As used herein, producing virions "in vitro" refers to producing virions outside of a cell, for instance, in a cell-free system, while producing virions "in vivo" refers to producing virions inside a cell, for instance, an *Eschericia coli* or *Pseudomonas aeruginosa* cell.

Bacteriophages

The system envisioned here is based on the properties of single-strand RNA bacteriophages [RNA Bacteriophages, in The Bacteriophages. Calendar, R L, ed. Oxford University Press. 2005]. The known viruses of this group attack bacteria as diverse as *E. coli, Pseudomonas* and *Acinetobacter*. Each possesses a highly similar genome organization, replication strategy, and virion structure. These include but are not limited to MS2, Qβ, R17, SP, PP7, GA, M11, MX1 and f2.

For purposes of illustration, the genome of a particularly well-characterized member of the group, called MS2, is shown in FIG. 1A. It is a single strand of (+)-sense RNA 3569 nucleotides long, encoding only four proteins, two of which are structural components of the virion. The viral particle is comprised of an icosahedral capsid made of 180 copies of coat protein and one molecule of maturase protein together with one molecule of the RNA genome. Coat protein is also a specific RNA binding protein. Assembly may possibly be initiated when coat protein associates with its specific recognition target an RNA hairpin near the 5'-end of the replicase cistron (FIG. 1B) as shown in SEQ ID NO: 1. The virus particle is then liberated into the medium when the cell bursts under the influence of the viral lysis protein. The formation of an infectious virus requires at least three components, namely coat protein, maturase and viral genome RNA, but experiments show that the information required for assembly of the icosahedral capsid shell is contained entirely within coat protein itself. For example, purified coat protein can form capsids in vitro in a process stimulated by the presence of RNA [Beckett et al., 1988, J. Mol. Biol 204: 939-47]. Moreover, coat protein expressed in cells from a plasmid assembles into a virus-like particle in vivo [Peabody, D. S., 1990, J Biol Chem 265: 5684-5689].

Coat Polypeptide

The coat polypeptide encoded by the coding region is typically at least 120, preferably, at least 125 amino acids in length, and no greater than 135 amino acids in length, preferably, no greater than 130 amino acids in length. It is expected that a coat polypeptide from essentially any single-stranded RNA bacteriophage can be used. Examples of coat polypeptides include but are not limited to the MS2 coat polypeptide (see, for example SEQ ID NO:2), R17 coat polypeptide (see, for example, Genbank Accession No $PO_{3612}$), PRR1 coat polypeptide (see, for example, Genbank Accession No. ABH03627), fr phage coat polypeptide (see, for example, Genbank Accession No. NP_039624), GA coat polypeptide (see, for example, Genbank Accession No. P07234), Qβ coat polypeptide (see, for example, Genbank Accession No. P03615), SP coat polypeptide (see, for example, Genbank Accession No P09673), and PP7 coat polypeptide (see, for example, Genbank Accession No PO363 0).

The coat polypeptides useful in the present invention also include those having similarity with one or more of the coat polypeptide sequences disclosed above. The similarity is referred to as structural similarity and is generally determined by aligning the residues of the two amino acid sequences (i.e., a candidate amino acid sequence and the amino acid sequence, for instance, of SEQ ID NO: 2) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO: 2. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbial Lett* 1999, 174:247-250), and available at http://www.ncbi.nlm.nih-.govlblast/b12seq/b12.html. Preferably, the default values for all BLAST 2 search parameters are used, including matrix=BLOSUM62; open gap penalty=11, extension gap penalty=1, gap xdropoff=50, expect=10, wordsize=3, and optionally, filter on. In the comparison of two amino acid sequences using the BLAST search algorithm, structural similarity is referred to as "identities." Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine.

Heterologous peptide sequences inserted into the coat polypeptide or polypeptide may be a peptide sequence that includes $Xaa_n$, wherein n is at least 4, at least 6, or at least 8 and no greater than 20, no greater than 18, or no greater than 16, and each Xaa is independently a random amino acid. Alternatively, the peptide fragment may possess a known functionality (e.g., antigenicity, immunogenicity). The heterologous sequence may be present at the amino-terminal end of a coat polypeptide, at the carboxy-terminal end of a coat polypeptide, or present elsewhere within the coat polypeptide. Preferably, the heterologous sequence is present at a location in the coat polypeptide such that the insert sequence is expressed on the outer surface of the capsid. In a particular embodiment, the peptide sequence may be inserted into the A-B loop regions the above-mentioned coat polypeptides. Examples of such locations include, for instance, insertion of the insert sequence into a coat polypeptide immediately following amino acids 11-17, or amino acids 113-117 of the coat polypeptide. In a most particular embodiment, the heterologous peptide is inserted at a site corresponding to
  (a) amino acids 11-17 or particularly 13-17 of MS-2, R17 and fr coat polypeptides;
  (b) amino acids 10-16 of GA coat polypeptide
  (c) amino acids 10-17 of QB and SP coat polypeptides;
  (d) amino acids 8-11 of PP7 coat polypeptides and
  (e) amino acids 9-17 of PRR1 coat polypeptides.

Alternatively, the heterologous peptide may be inserted at the N-terminus or C-terminus of the coat polypeptide.

In order to determine a corresponding position in a structurally similar coat polypeptide, the amino acid sequence of this structurally similar coat polypeptide is aligned with the sequence of the named coat polypeptide as specified above in the section entitled Amino Acid Homology. For example, the corresponding position of a coat polypeptide structurally similar to MS-2 coat polypeptide is aligned with SEQ ID NO:2. From this alignment, the position in the other coat polypeptide which corresponds to a given position of SEQ ID NO: 1 can be determined.

In a particular embodiment, the coat polypeptide is a single-chain dimer containing an upstream and downstream subunit Each subunit contains a functional coat polypeptide sequence. The heterologous peptide may be inserted ton the upstream and/or downstream subunit at the sites mentioned herein above, e.g., A-B loop region of downstream subunit. In a particular embodiment, the coat polypeptide is a single chain dimer of an MS2 coat polypeptide which may have a sequence depicted in SEQ ID NO:12.

Preparation of Transcription Unit

Figure 2:
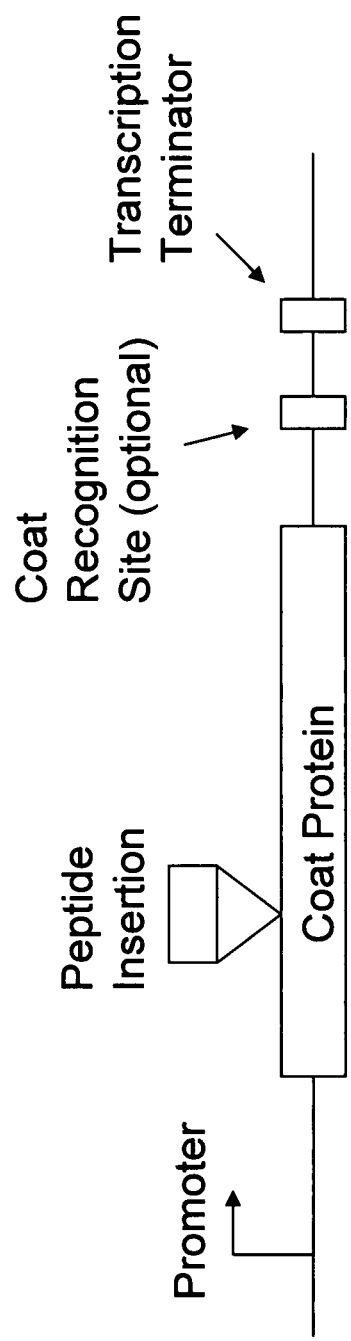
FIG. 2 shows a schematic representation of one design for a transcription/translation template capable of producing RNA-bacteriophage-like particles displaying foreign peptides on their surface while encapsidating the RNA that encodes the coat polypeptide-peptide fusion.

The transcription unit of the present invention comprises an expression regulatory region, (e.g., a promoter), a sequence encoding a coat polypeptide and transcription terminator. The RNA polynucleotide may optionally include a coat recognition site (also referred to a "packaging signal", "translational operator sequence", "coat recognition site"). A most particular embodiment is shown in FIG. 2. Alternatively, the transcription unit may be free of the translational operator sequence. The promoter, coding region, transcription terminator, and, when present, the coat recognition site, are generally operably linked. Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by me coding region encoding the coat polypeptide Examples of such promoters are known in the art and include, for instance, T7, T3, and SP6 promoters.

The nucleotide sequences of the coding regions encoding coat polypeptides described herein are readily determined. An example of the class of nucleotide sequences encoding one of the coat polypeptides described herein is nucleotides 4080-4470 of SEQ ID NO:3. These classes of nucleotide sequences are large but finite, and the nucleotide sequence of each member of the class can be readily determined by one skilled in the art by reference to the standard genetic code.

Furthermore, the coding sequence of an RNA bacteriophage single chain coat polypeptide comprises a site for insertion of a heterologous peptide as well as a coding sequence for the heterologous peptide itself. In a particular embodiment, the site for insertion of the heterologous peptide is a restriction enzyme site.

Figure 3:
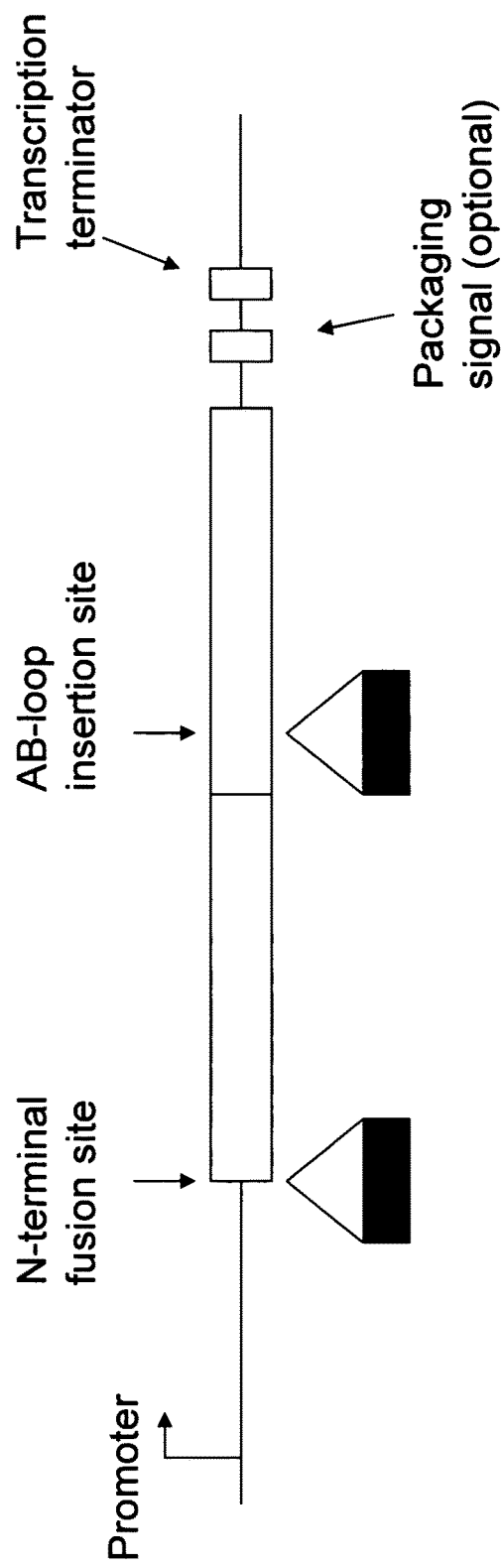
FIG. 3 shows principal features of a VLP transcription unit.

In a particular embodiment, the coding region encodes a single-chain dimer of the coat polypeptide. In a most particular embodiment, the coding region encodes a modified single chain coat polypeptide dimer, where the modification comprises an insertion of a coding sequence at least four amino acids at the insertion site. A schematic diagram of a particular embodiment of such a transcription unit is shown in FIG. 3. The transcription unit may contain a bacterial promoter, such as a lac promoter or it ma contain a bacteriophage promoter, such as a T7 promoter and optionally a T7 transcription terminator.

In addition to containing a promoter and a coding region encoding a fusion polypeptide, the RNA polynucleotide typically includes a transcription terminator, and optionally, a coat recognition site. A coat recognition site is a nucleotide sequence that forms a hairpin when present as RNA. This is also referred to in the art as a translational operator, a packaging signal, and an RNA binding site. Without intending to be limiting, this structure is believed to act as the binding site recognized by the translational repressor (e.g., the coat polypeptide), and initiate RNA packaging. The nucleotide sequences of coat recognition sites are known in the art and include, for instance, nucleotides in SEQ ID NO:1 (see FIG. 1B). Other coat recognition sequences have been characterized in the single stranded RNA bacteriophages R17, GA, Qβ, SP, and PP7, and are readily available to the skilled person. Essentially any transcriptional terminator can be used in the RNA polynucleotide, provided it functions with the promoter. Transcriptional terminators are known to the skilled person, readily available, and routinely used.

Synthesis

As will be described in further detail below, the VLPs of the present invention may be synthesized in vitro in a coupled cell-free transcription/translation system. Alternatively VLPs could be produced in vivo by introducing transcription units into bacteria, especially if transcription units contain a bacterial promoter.

VLP Populations

As noted above, the invention is directed to VLP populations or libraries. The terms "population" and "libraries" in the instant specification are used interchangeably and are thus deemed to be synonymous. In one particular embodiment, the library may be a random library; in another embodiment, the library is an antigen fragment library, a library of fragments derived from an antigenic polypeptide.

Random Libraries (Populations)

Oligonucleotides encoding peptides containing may be prepared. In one particular embodiment, In a particular embodiment, the triplets encoding a particular amino acid has the composition NNS where N is A, G, C or T and S is G or T or alternatively NNY where N is A, G, C, or T and Y is C or T. In order to minimize the presence of stop codons, peptide libraries can be constructed using oligonucleotides synthesized from custom trinucleotide phosphoramidite mixtures (available from Glen Research, Inc.) designed to more accurately reflect natural amino acid compositions and completely lacking stop codons.

Figure 4:
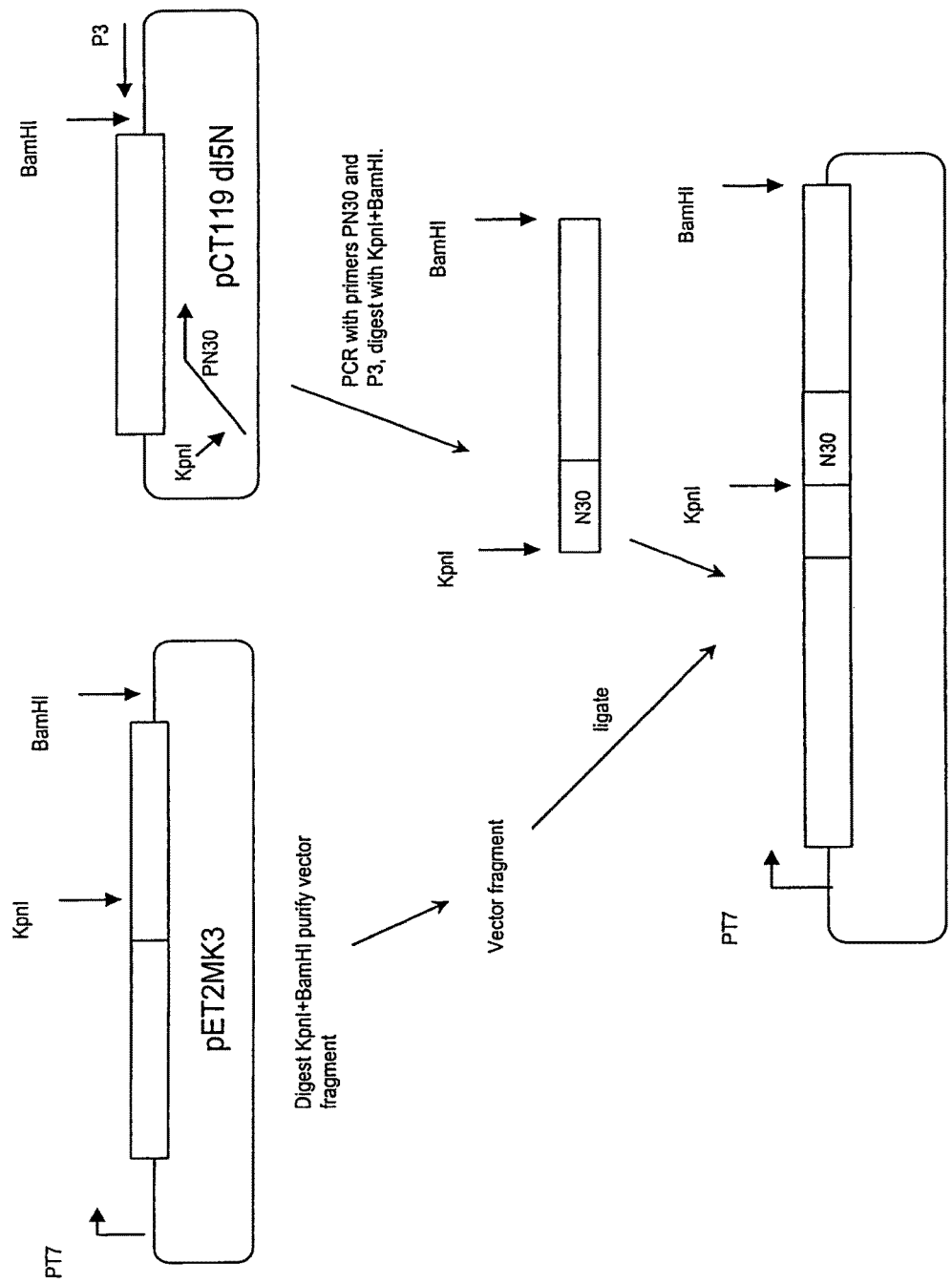
FIG. 4 shows a method for the construction of a library of 10-amino acid insertions in the downstream-most AB-loop of the single-chain dimer. The procedure starts with plasmids pET2MCTK3 (see FIG. 16) and pCT119c15N (see FIG. 17) and produces a vector fragment by restriction enzyme digestion, and an insert fragment by PCR. One primer (P3 having the sequence 5'-GTTGTAAAACGACG-GCCAGT-3' depicted in SEQ ID NO:13 anneals downstream of a unique BamHI site and the other (PN30) having the sequence depicted in SEQ ID NO:14, 5'-CGCGGTAC-CNNSNNSNNSNNSNNSNNSNNSNNSNNSNNSGGAA-CTGGCGACGTGA CTGTC-3', where S=G or C and N=A, C,G,T primes immediately downstream of the plasmid's Kpn I site (eliminating it) and introduces a random 30-nucleotide sequence and a new Kpn I site at the 5'-end end of the new fragment. These fragments are joined by ligation and introduced into E. coli by electroporation to produce a complex library of random peptide sequences.

FIG. 4 shows a simple scheme for producing a library of 10-amino acid insertions in the AB-loop of the C-terminal copy of a single-chain dimer. As shown in FIG. 4, a KpnI site engineered into codons 14 and 15 of the downstream coat sequence of the single-chain dimer. In another embodiment, alternate plasmids may be constructed which take advantage of a naturally occurring SalI site at codons 11 and 12. The SalI sites may be removed from all other locations in the plasmid, including the one normally present in the upstream half of the single-chain dimer, so now a unique SalI site is found in the downstream half. In such an instance, the PN30 primer may have the sequence 5'-CCCCGTCGACAATG-GCNNSNNSNNSNNSNNSNNSNNSNNSGGAACTGGC-GACGTG ACTGTC-3' (SEQ ID NO: 15) and would result in the insertion of random 8-amino acid sequences between amino acids 13 and 14. A primer of sequence 5'-CCCCGTC-GACAATGGCNNSNNSNNSNNSNNSNNSNNSNNG-GCGACGTGACTGTCG CCCCA-3' (SEQ ID NO: 16) inserts random 8-amino acid peptides between amino acids 13 and 16, and 5'-CCCCGTCGA-CAATNNSNNSNNSNNSNNSNNSNNSNNSGACGT-GACTGTCGCCCCAA GC-3' (SEQ ID NO:17) puts them between amino acids 12 and 17.

Antigenic Libraries

An alternative strategy takes advantage of the existence of a cloned antigen gene or pathogen genome to create random antigen fragment libraries. The idea is to randomly fragment the gene (e.g. with DNase1) to an appropriate average size (e.g. ~30 bp), and to blunt-end ligate the fragments to an appropriate site in coat polypeptide. In a particular embodiment, a restriction site may be inserted into the AB-loop or N-terminus of the coat polypeptide). Only a minority of clones will carry productive inserts, because they shift reading frame, introduce a stop codon, or receive an insert in antisense orientation, Any expression vector may in one embodiment contain a marker to pre-select clones with intact coat coding sequences. For example, GalE-strains of *E. coli* are defective for galactose kinase and accumulate a toxic metabolite when β-galactosidase is expressed in the presence of the galactose analogue, phenyl-β,D-galactoside (PGal). Subjecting a random antigen-fragment library to selection for translational repressor function in the GalE-strain CSH41 F-containing pRZ5, a plasmid that fuses the MS2 replicase cistron's translational operator to lacZ will eliminate most undesired insertions by enriching the library for those that at least maintain the coat reading-frame.

Synthesis

In a particular embodiment, the populations of the present invention may be synthesized in a coupled in vitro transcription/translation system using procedures known in the art (see, for example, U.S. Pat. No. 7,008,651 Kramer et al., 1999, Cell-free coupled transcription-translation systems from *E. coli*, In. Protein Expression. A Practical Approach, Higgins and Hames (eds.), Oxford University Press). In a particular embodiment, bacteriophage T7 (or a related) RNA polymerase is used to direct the high-level transcription of genes cloned under control of a T7 promoter in systems optimized to efficiently translate the large amounts of RNA thus produced [for examples, see Kim et al., 1996, Eur J Biochem 239: 881-886; Jewett et al., 2004, Biotech and Bioeng 86: 19-26].

It is possible in a mixture of templates, particularly in the population of the present invention, different individual coat polypeptides, distinguished by their fusion to different peptides, could presumably package each other's mRNAs, thus destroying the genotype/phenotype linkage needed for effective phage display. Moreover, because each capsid is assembled from multiple subunits, formation of hybrid capsids may occur. Thus, in one preferred embodiment, when preparing the populations or libraries of the present invention, one or more cycles of the transcription/translation reactions be performed in water/oil emulsions [Tawfik et al., 1998, *Nat Biotechnol* 16: 652-6]. In this now well-established method, individual templates are segregated into the aqueous compartments of a water/oil emulsion. Under appropriate conditions huge numbers of aqueous microdroplets can be formed, each containing on average a single DNA template molecule and the machinery of transcription/translation. Because they are surrounded by oil, these compartments do not communicate with one another. The coat polypeptides synthesized in such droplets should associate specifically with the same mRNAs which encode them, and ought to assemble into capsids displaying only one peptide. After synthesis, the emulsion can be broken and the capsids recovered and subjected to selection. In one particular embodiment, all of the transcription/translation reactions are performed in the water/oil emulsion. In another embodiment, mixed capsids may be obtained in one or more cycles of transcription/translation reactions but subsequent cycles of the transcription/translation reaction, particularly beginning with the second, third, fourth or fifth cycle, are carried out in the water/oil emulsion.

Uses of VLPs and VLP Populations

There are a number of possible uses for the VLPs and VLP populations of the present invention. As will be described in further detail below, the VLPs may be used to as immunogenic compositions, particularly vaccines, drug delivery devices, biomedical imaging agents and self-assembling nanodevices. The VLP populations of the present invention may be used to select suitable vaccine candidates.

Selection of Vaccine Candidates

Figure 5:
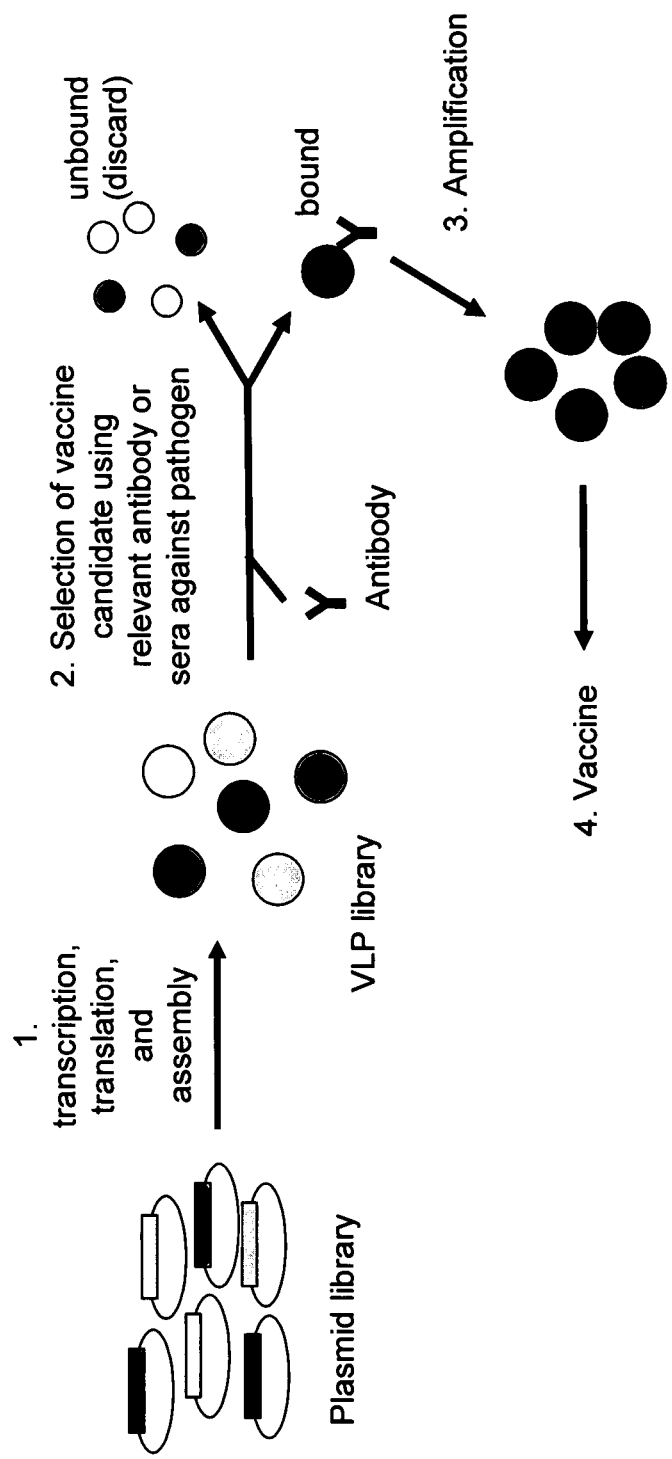
FIG. 5 shows a strategy for rapid vaccine discovery.

The VLP populations or libraries of the present invention may be used to select vaccine candidates. The libraries may be random or antigenic libraries. A particular embodiment is outlined in FIG. 5. Libraries of random or alternatively antigen-derived peptide sequences are displayed on the surface of VLPs, and specific target epitopes, or perhaps mimitopes are then isolated by affinity-selection using antibodies. Since the VLPs encapsidate their own mRNAs, sequences encoding them (and their guest peptides) can be recovered by reverse transcription and PCR. Individual affinity-selected VLPs are subsequently cloned, over-expressed and purified.

Techniques for affinity selection in phage display are well developed and are directly applicable to the VLP display system of the present invention. Briefly, an antibody (or antiserum) is allowed to form complexes with the peptides on VLPs in a random sequence or antigen fragment display library. Typically the antibodies will have been labeled with biotin so that the complexes can be captured by binding to a streptavidin-coated surface, magnetic beads, or other suitable immobilizing medium. After washing, bound VLPs are eluted, and RNAs are extracted from the affinity-selected population and subjected to reverse transcription and PCR to recover the coat-encoding sequences, which are then recloned and subjected to further rounds of expression and affinity selection until the best-binding variants are obtained. A number of schemes for retrieval of RNA from VLPs are readily imagined. One attractive possibility is to simply capture biotin-mAb-VLP complexes in streptavidin coated PCR tubes, then thermally denature the VLPs and subject their RNA contents directly to RT-PCR. Many obvious alternatives exist and adjustments may be required depending on considerations such as the binding capacities of the various immobilizing media. Once the selected sequences are recovered by RT-PCR it is a simple matter to clone and reintroduce them into E. coli, taking care at each stage to preserve the requisite library diversity, which, of course, diminishes with each round of selection. When selection is complete, each clone can be over-expressed to produce a VLP vaccine candidate.

Immunogenic Compositions

As noted above, the VLPs identified by the screening procedures of the present invention may be used to formulate immunogenic compositions, particularly vaccines. The vaccines should be in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition or disorder. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide and modified muramyl dipeptide.

Optionally, the vaccine of the present invention additionally includes an adjuvant which can be present in either a minor or major proportion relative to the compound of the present invention.

Targeted Drug Delivery

The MS2 VLP is a hollow sphere with an internal diameter on the order of 20 nm. In a particular embodiment, the VLP comprises the drug, e.g., a protein toxin to be delivered and optionally a ligand that binds to cell-type specific receptors. The internal composition of such a particle may be controlled by specifically loading it, for example, with a protein toxin like ricin, by coupling it to a synthetic translational operator mimic. By conferring the ability to bind cell type-specific receptors to the outer surface of such particles, it is possible to target delivery of the toxin (or other drug) to selected cell types.

Biomedical Imaging Agents

In the same way that drugs can be targeted to specific cell types, so could contrast agents for magnetic resonance imaging be delivered to specific cells or tissues, potentially increasing enormously the diagnostic power of MRI. In fact, MS2 particles have already been labeled with gadolinium to greatly increase MRI contrast [Anderson et al., 2006, *Nano Letters* 6(6), 1160-1164]. Thus, in a particular embodiment, such particles could be targeted to specific sites by displaying appropriate receptor-specific peptides on their surfaces.

Self-Assembling Nano-Devices

The VLPs of the present invention may comprise peptides with affinity for either terminus of a filamentous phage particle that display metal binding proteins. A VLP with affinity for either terminus of a filamentous phage particle would create the possibility of connecting these spheres (and whatever they contain) to the ends of filamentous phage nanowires. Alternatively, the VLPs may display metal-binding peptides (e.g. gold and zinc) so that arrays with unusual electrical and optical properties may be obtained. Alternatively, VLPs with improved ability to self-assemble into these arrays may be produced by displaying peptides with affinity for a particular surface, or that alter the self-association properties of the VLPs themselves.

EXAMPLES

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention.

Example 1

In Vitro Expression of MS2 Coat Protein

Figure 6:
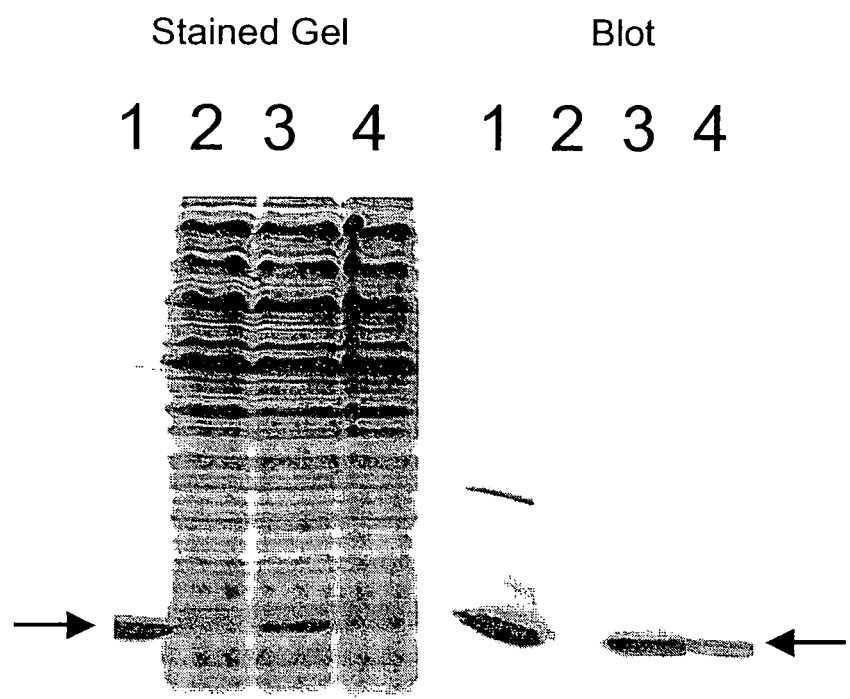
FIG. 6 shows the SDS-polyacrylamide gel electrophoresis of the products of in vitro transcription/translation.
Figure 7:
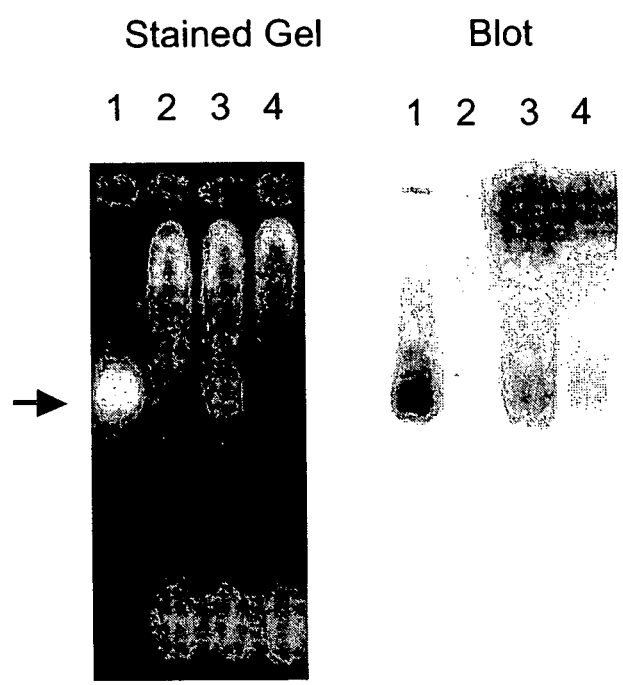
FIG. 7 shows an agarose gel electrophoresis to detect capsids produced by transcription/translation.
Figure 20:
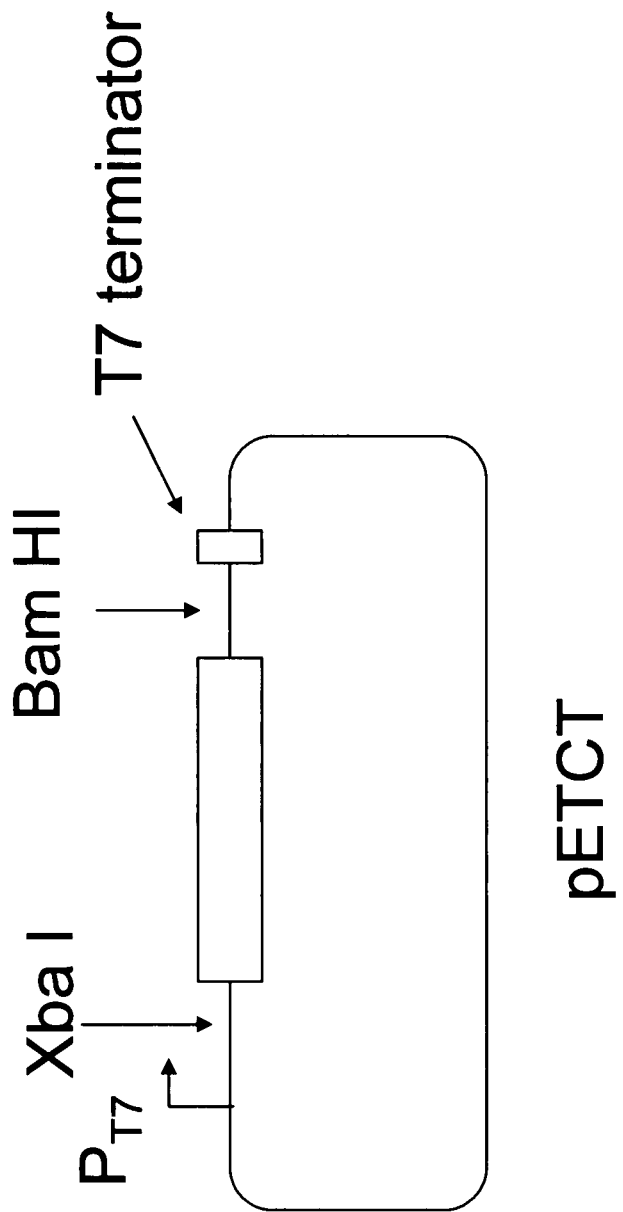
FIG. 20 shows a schematic diagram of pETCT depicted in SEQ ID NO:21. pETCT contains a T7 promoter which drives transcription of the wild-type coat gene and a T7 transcription terminator downstream of coat.

Extracts of *E. coli* cells capable of carrying out transcription and translation in vitro were described more than 30 years ago [Zubay G., 1973, *Annu Rev Genet* 7: 267-87], but recent improvements have greatly increased their ability to produce useful quantities of product (see Kramer et al., Cell-free coupled transcription-translation systems from *E. coli*, In.: Protein Expression. A Practical Approach, Higgins and Hames (eds.), Oxford University Press (1999) for example). Originally, these systems relied on the presence of endogenous *E. coli* RNA polymerase to transcribe genes from relatively weak promoters, and it was necessary to utilize the incorporation of radioactive amino acids even to detect the relatively low-level of protein they typically synthesized. Modern systems use bacteriophage T7 (or a related) RNA polymerase to direct the high-level transcription of genes cloned under control of a T7 promoter in systems optimized to efficiently translate the large amounts of RNA thus produced [for examples, see Kim et al., 1996, *Eur J Biochem* 239: 881-886; Jewett et al., 2004, *Biotech and Bioeng* 86: 19-26]. An example result is shown in FIG. 6. Here an in vitro transcription/translation system (in this case the Activepro system of Ambion, Inc.) was programmed with plasmids expressing MS2 coat protein from a T7 promoter, and the proteins were separated by SDS-polyacrylamide gel electrophoresis. Lane 3 shows the plasmid called pETCT (FIG. 20) directed the synthesis of coat protein in sufficient quantity that it was easily visualized in the stained gel. Probing a Western blot of a similar gel with anti-MS2 serum confirmed the product's identity (FIG. 6). In lane 4 is shown the protein synthesized using pETMCT, a plasmid differing from pETCT by the inclusion of the translational operator downstream of the coat coding sequence. It appears that pETMCT synthesizes significantly less coat protein than pETCT. Still, the product is easily detected. Electrophoresis of the transcription/translation products in an agarose gel, where correctly assembled viruses and virus-like particles have a distinctive mobility, reveals material having the mobility and immunological reactivity characteristic of MS2 capsids (FIG. 7). Although much of the coat protein seems to remain unassembled, significant quantities of capsids are present in both samples. Furthermore, the appearance of an ethidium bromide stained capsid band indicates that the particles package RNA.

Example 2

Development of MS2 VLP Display

A-B Loop Insertion

Figure 8:
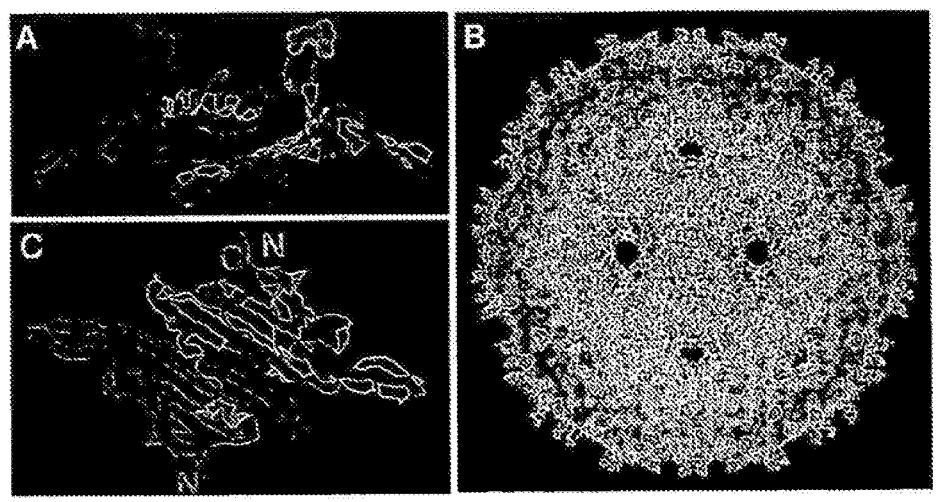
FIG. 8. (A) Structure of the MS2 coat polypeptide dimer seen edge-on. The two polypeptide chains are colored red and blue and the AB-loops are emphasized by showing amino acids 13, 14 and 15 in a space-filling representation. (B) The MS2 VLP with coat polypeptide subunits in green and the AB-loops in red space-fill to illustrate their arrangement and exposure on the VLP surface. (C) Structure of the MS2 coat polypeptide dimer as it would be viewed from outside the capsid. Note the proximity of the N- and C-termini of the dimer's two polypeptide chains.

The AB-loop is a 3-residue turn connecting coat protein's A and B beta-strands (FIG. 8). Peptides inserted here are highly accessible and, because they are tethered at both ends, conformationally constrained. Since many epitopes in their native environments are found in surface loops, this is a natural location for peptide display. Capsid geometry dictates that the AB-loop is encountered at regular intervals of roughly 30 angstroms, so peptides inserted here form dense repetitive arrays. Efforts to produce active AB-loop insertions have met with mixed success [Stockley et al., 2000, *Methods Enzymol* 326:551-569]. In some cases, insertions were tolerated, but when they were not, the protein failed to fold correctly and either aggregated in inclusion bodies or was proteolyically degraded. In the instant example, a solution is described.

Two examples are presented to illustrate the point. First, to facilitate construction of insertions introduced two silent mutations were introduced in coat protein codons 14 and 15 to produce a convenient and unique Kpn I site within the AB-loop-encoding sequence. Two different 10-amino acid peptides were inserted here. The first, called ECL2, is derived from extracellular loop-2 of the HIV co-receptor, CCR5. The other (V3) is from the third variable loop of the HIV envelope glycoprotein, gp120. Both insertions interfered with coat protein folding. In fact, the proteins failed even to accumulate in significant quantities apparently because they were degraded. These disappointing results would argue against the use of MS2 for epitope display were it not for a simple trick that reverses these folding/stability defects. Inspection of the 3-dimensional structure of the coat protein dimer (FIG. 9) reveals the close physical proximity of the N-terminus of one chain to the C-terminus of the other. These ends are covalently linked by duplicating the coat sequence and fusing the two copies into one long reading frame, thus producing "dimers" whose two halves are synthesized as a single polypeptide chain. This so-called single-chain dimer has all the functions of normal coat protein; it folds correctly, represses translation by specifically binding the translational operator of the replicase cistron, and assembles into a normal VLP. It was originally constructed to analyze the RNA binding site of mutant coat proteins in heterodimer complementation experiments [Powell et al., 2001, *BMC Mol Biol* 2:6; Peabody et al., 1999, *J Biol Chem* 274(36):25403-25410; Peabody et al., 1996, Nucleic Acids Res 24(12):2352-2359], but while performing that work it was noticed that the single-chain dimer is substantially more stable thermodynamically than its parent. It is considerably more resistant to thermal and chemical denaturation and is dramatically more tolerant of various mutational perturbations [for examples, see Peabody et al., 1999, *J Biol Chem* 274(36):25403-25410] and Peabody et al., 1997, *Arch Biochem Biophys* 347(1):85-92]. Although inserting the ECL2 or V3 epitope into the AB-loop of wild-type coat protein disrupts its ability to properly fold, both peptides are tolerated when inserted into one AB-loop of a single chain dimer, They are produced as soluble proteins in normal yields, they fold correctly, and they assemble into VLPs with the foreign epitopes on their outer surfaces.

Figure 12:
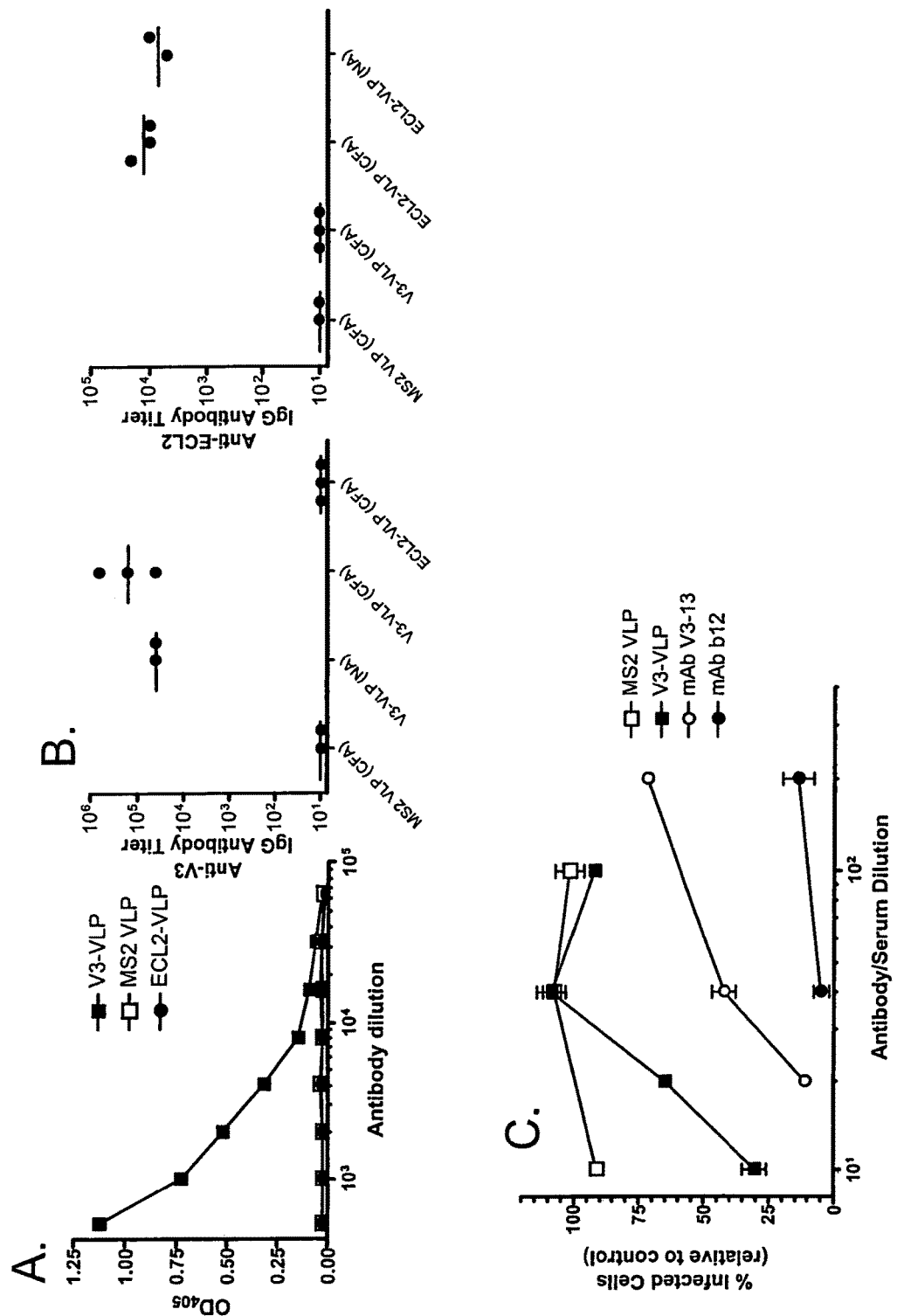
FIG. 12 (B) IgG antibody responses in C57B1/6 mice immunized with wild-type MS2 VLPs, V3-VLPs, or ECL2-VLPs. End-point dilution ELISA titers against a peptide representing HIV gp120 V3 (left panel), or a peptide representing the CCR5 ECL2 undecapeptidyl arch (UPA) (right panel) in serum from mice immunized three times with each VLP type. VLPs were administered either in the presence of complete Freund's adjuvant (CFA) or without adjuvant (NA). Results are from sera obtained 7 days after the third vaccination. Each data point represents the antibody titer from an individual mouse. Lines represent the geometric mean titer for each group.
Figure 12:
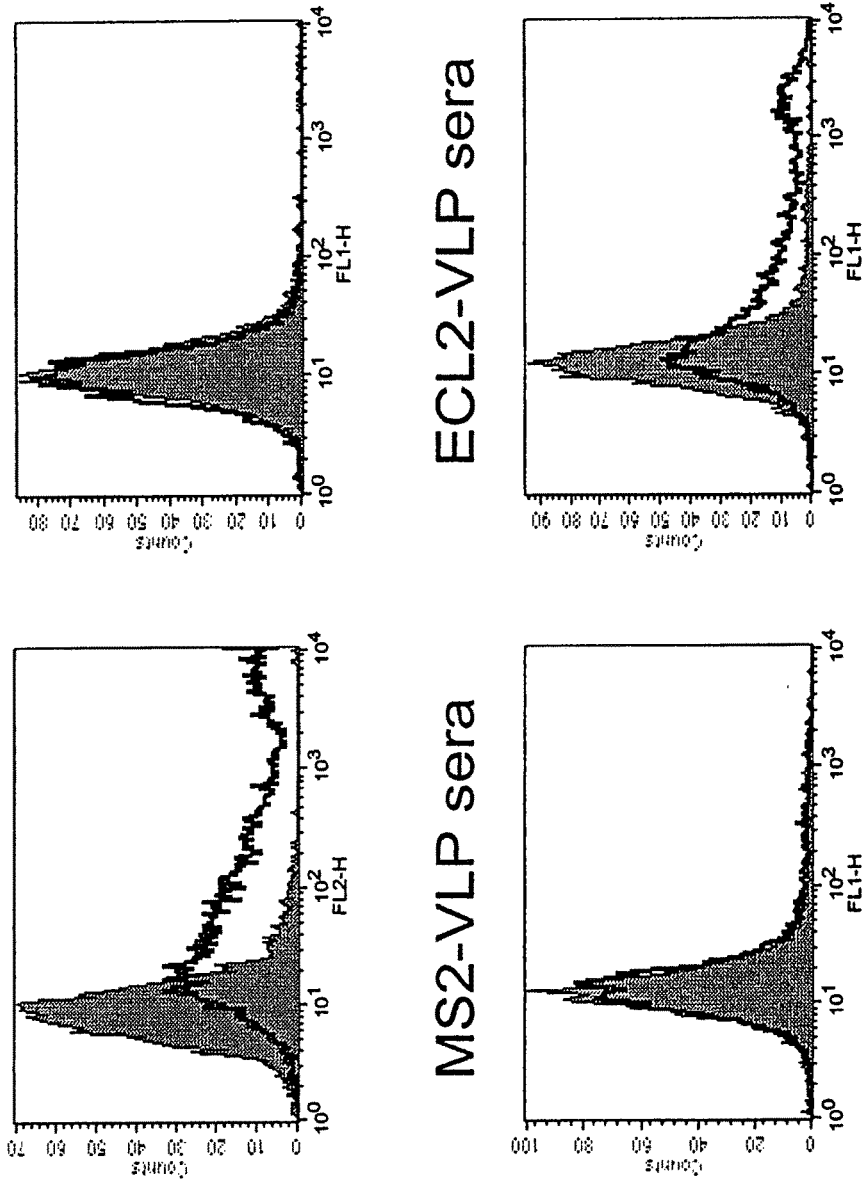
Figure 13:
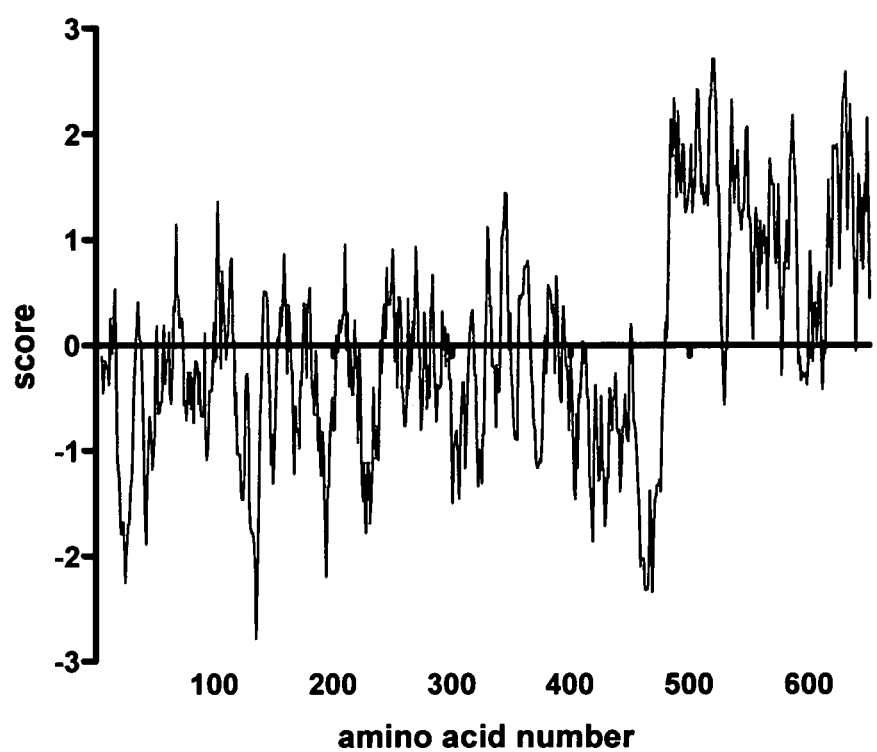
FIG. 13 shows a hydrophobicity plot by the method of Kyte and Doolittle of a hypothetical protein produced by arbitrarily grouping all the random peptide sequences that resulted in a repressor-competent coat protein (residues 1-482) and those that interfered with coat function (residues 483-662). Note the sharp transition to higher hydrophobicity at about amino acid 483.
Figure 14:
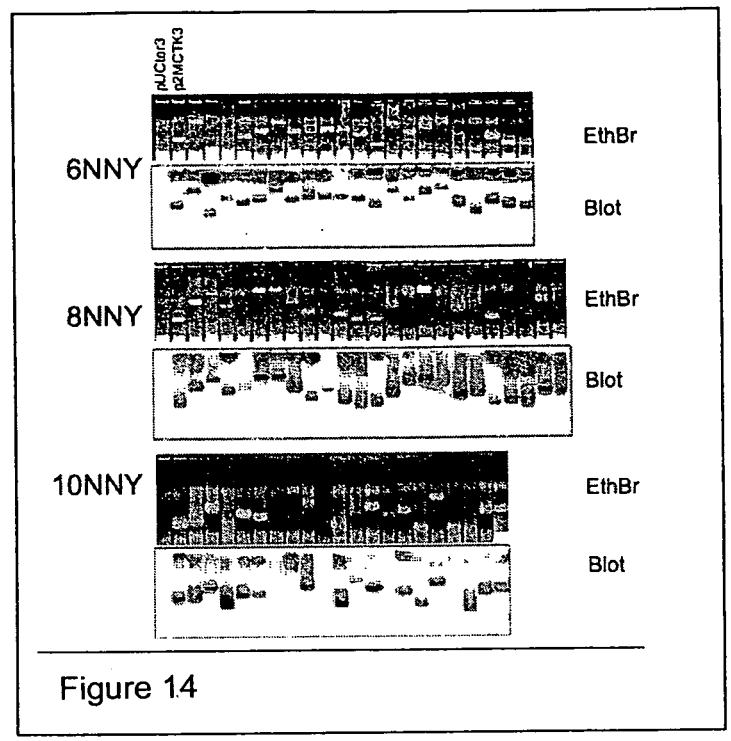
FIG. 14 shows electrophoresis on agarose gel of VLPs found in crude lysates of cells containing various recombinant plasmids, each of which produces a coat protein with a different random 6-, 8- or 10-amino acid insertion. The first two lanes of each gel are controls: pUCter3 produces no coat protein, while p2MCTK3 is the single-chain dimer construct without a peptide insertion. Ethidium bromide-stained gels (upper half of each set) and blots probed with anti-MS2 serum (lower half of each set) are shown.
Figure 15:
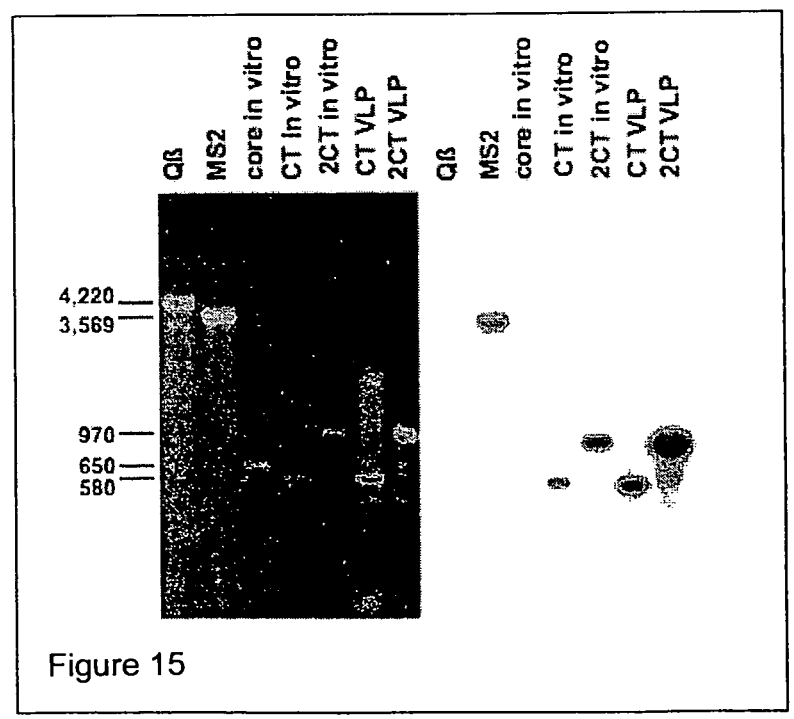
FIG. 15 shows electrophoresis (left panel) and Northern Blot analysis (right panel) of VLP-encapsulated RNAs. CT VLP and 2CT VLP refer to the RNAs extracted from conventional and single-chain dimer VLPs respectively. CT in vitro and 2CT in vitro refer to the products of transcription in vitro of the same plasmids that produced the VLPs. The in vitro transcription product of a similar plasmid containing HCV core sequences (core in vitro) was also run for comparison. MS2 and Qβ RNAs were extracted from the purified phages.
Figure 16:
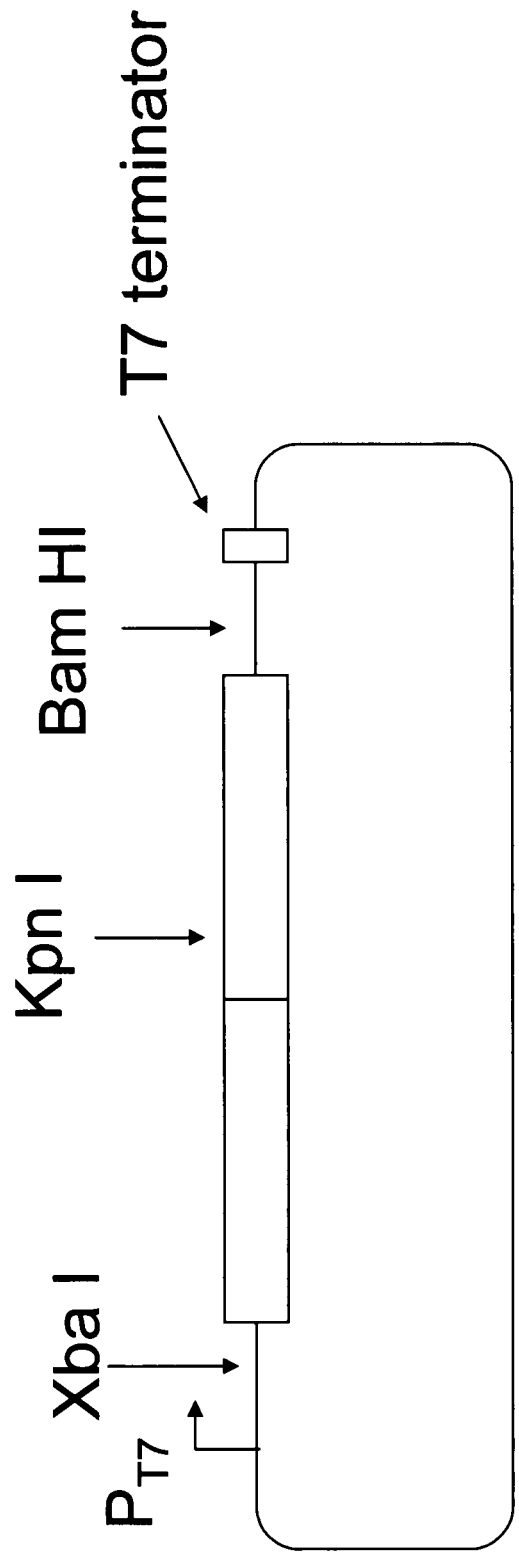
FIG. 16 shows a schematic diagram of pET2MK3 depicted in SEQ ID NO:18. pET2MK3 has the coat sequence of p2MK3 under T7 promoter control. It has a T7 transcription terminator, but no packaging signal.
Figure 17:
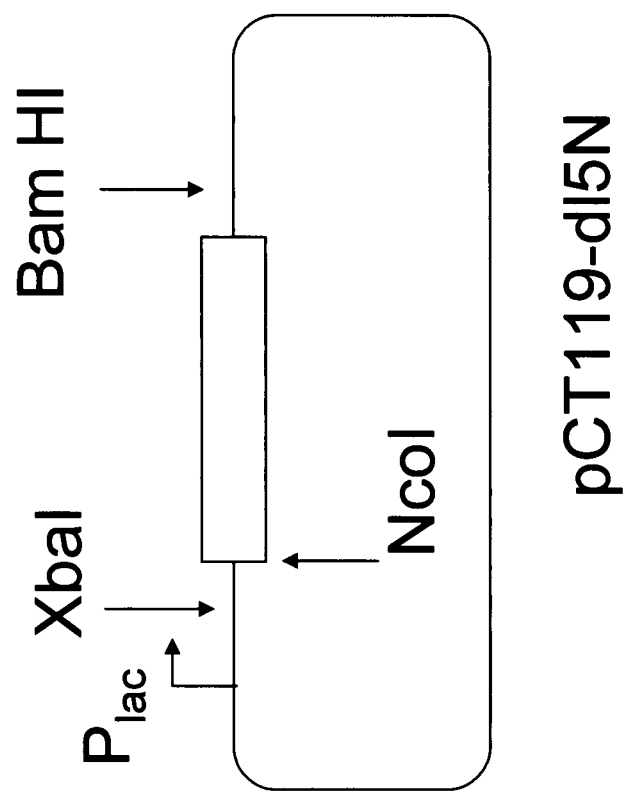
FIG. 17 shows a schematic diagram of pCT19-d15N depicted in SEQ ID NO:19. This plasmid has the coat sequence under lac promoter control. It serves as a convenient source of template for PCR reactions to generate random sequence peptide libraries.

Although the density of displayed epitopes is reduced by half when presented in only one AB-loop of the single-chain dimer these particles retain their high immunogenicity. Immunization of mice with MS2-V3-VLPs, even in the absence of exogenous adjuvant, induced high titer antibodies able to recognize the V3 peptide (FIG. 12). Further, the anti-V3 sera protected cells against HIV infection in vitro, The MS2-ECL2-VLPs elicited a similarly strong immune response to CCR5. These results suggested that the single-chain dimer might provide the means to produce potently immunogenic MS2 VLPs tolerant of a wide range of peptide insertions in the AB-loop.

In addition to those described above, several other designed peptides have been inserted into one AB-loop of a single chain MS2 coat protein dimmer, and in nearly every case translational repression and capsid assembly activities remained intact, suggesting a broad tolerance of the single-chain dimmer to such insertions.

N-Terminal Fusions

Figure 9:
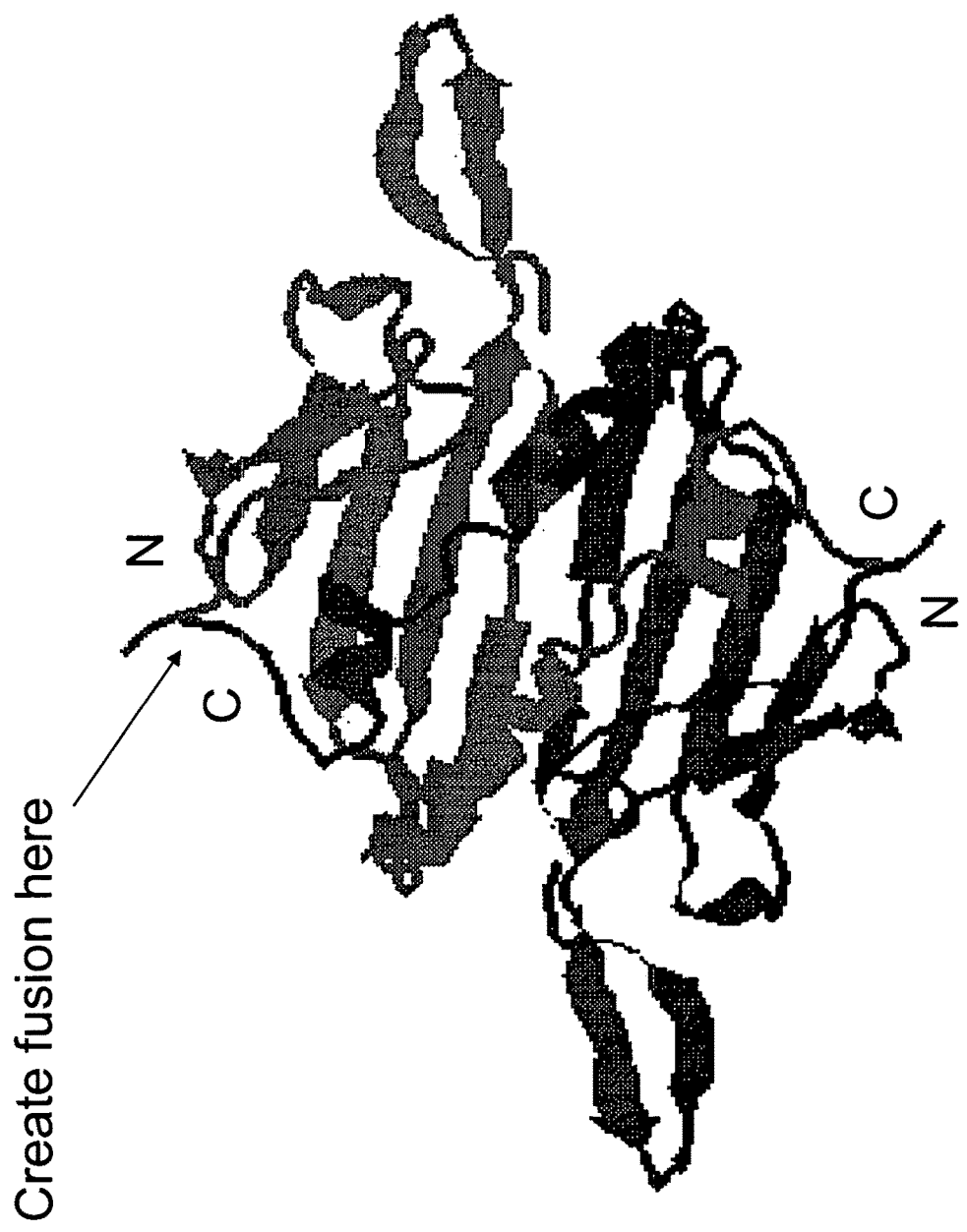
FIG. 9 shows the single-chain dimer was constructed by genetic fusion of the coat polypeptide-s two identical polypeptide chains.

The N-terminus presents an alternative site of peptide fusion. FIGS. 8 and 9 show the locations of the N-termini and demonstrates their accessibility at the VLP surface. Three different specific fusions were produced, including an 8-amino acid flag epitope, a 20-amino acid 6×His-tag with a thrombin cleavage sequence, and a 23-amino acid biotin ligase target peptide. In each case, the protein remains functional for translational repression, indicating that it folds correctly into the dimeric structure necessary for specific RNA binding. However, the presence of the fusion tends to interfere with assembly of dimers into VLPs, presumably because the elongated N-termini of three different subunits crowd each other at quasi-3-fold symmetry axes in the capsid. But again the single-chain dimer corrects the defect, because reducing by half the number of N-termini apparently diminishes crowding and permits assembly. The VLPs thus produced display the foreign peptide on their outer surfaces [Peabody, 1997, Arch Biochem Biophys 347(1):85-92]. Functional coat protein-GFP fusions have also been produced for various purposes, indicating that fusion even of large proteins permits coat protein folding. Thus, the N-terminus provides a second site suitable target for peptide display.

The N-terminus provides a means to display conformationally unconstrained peptides, which, because they are free to adopt a wider range of conformations, may increase the likelyhood that a random sequence library contains a peptide capable of recognizing any particular antibody.

Example 3

Immunogenic Display of Diverse Peptides on Virus-Like Particles of RNA Bacteriophage MS2

In the instant example, a platform is described for vaccine development based on the VLPs of RNA bacteriophage MS2. It serves for the engineered display of specific peptide sequences, but also allows the construction of random peptide libraries from which specific binding activities can be recovered by affinity selection. Peptides representing the V3 loop of HIV gp120 and the ECL2 loop of the HIV coreceptor, CCR5, were inserted into a surface loop of MS2 coat protein. Both insertions disrupted coat protein folding and VLP assembly, but these defects were efficiently suppressed by genetically fusing coat protein's two identical polypeptides into a single-chain dimer. The resulting VLPs displayed the V3 and ECL2 peptides on their surfaces where they showed the potent immunogenicity that is the hallmark of VLP-displayed antigens. Experiments with random-sequence peptide libraries show the single-chain dimer to be highly tolerant of 6-, 8- and 10-amino acid insertions. Not only do MS2 VLPs support the display of a wide diversity of peptides in a highly immunogenic format, but they also encapsidate the mRNAs that direct their synthesis, thus establishing the genotype/phenotype linkage necessary for recovery of affinity selected sequences. The single-chain MS2 VLP therefore unites in a single structural platform the selective power of phage display with the high immunogenicity of VLPs.

Materials and Methods

Plasmid Construction

Figures 10A, 10B:
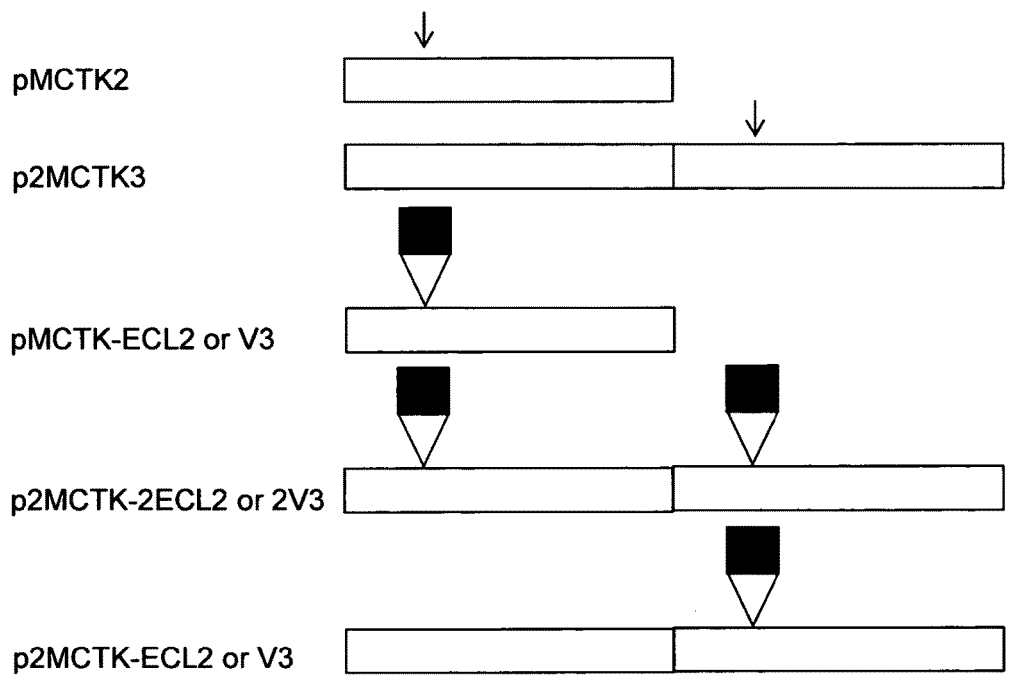
FIG. 10(A) shows arrangements of the coat polypeptide reading frames of the plasmids used in this study. All express coat polypeptide from the lac promoter. pMCTK is similar to the previously described pCT119 Peabody 1990, J. Biol. Chem. 265: 5684-5689), but has silent mutations in codons 14 and 15 that introduce the Kpn I site (indicated by arrows). p2MCTK3 expresses a single-chain dimer version of the protein with the Kpn I site in the C-terminal half of the single-chain dimer. Black boxes represent the ECL2 or V3 peptide insertions in the various plasmid derivatives.
FIG. 10(B) Amino acid sequences (single-letter code) of the ECL2 and V3 peptides (top lines) and of the annealed oligonucleotides that encode them (SEQ ID NOS: 4-9).

A PCR overlap extension method [Higuchi et al., 1988, Nucleic Acids Res 16(15):7351-67] introduced two silent nucleotide changes in codons 14 and 15 of the coat sequence and a unique KpnI site into the MS2 coat gene of pMCT, a plasmid nearly identical to the previously described pCT119 [Peabody, 1990, J Biol Chem, 265(10):5684-9]. The new construct is called pMCTK2 (see FIG. 18). Synthetic duplex oligonucleotides (from Integrated DNA Technologies, see FIG. 10B) encoding the ECL2 and V3 peptides were inserted into the Kpn I site (SEQ ID NOS:4-9). DNA sequence analysis of the resulting recombinants confirmed the presence of the designed sequences. These plasmids were called pMCTK-ECL2 and pMCTK-V3 (FIG. 10A).

The various single-chain dimer versions of the pMCTK-ECL2 and -V3 recombinants (FIG. 10A) were produced by duplication of the wild-type and recombinant coat sequences. Briefly, the upstream half was produced by PCR amplification using a 5' primer that anneals to plasmid sequences upstream of the coat sequence, and a downstream primer that creates a Bgl I site at the 3'-end of the coding sequence. This fragment was digested at the new Bgl I site and at the Hind III site in the upstream plasmid sequence. The downstream half was synthesized using a primer that creates a Bgl I site at the 5'-end of the coding sequence, and a 3'-primer that anneals to plasmid sequences downstream of coat. This fragment was digested at the Bgl I site at the 5'-end of this PCR fragment and at a Bam HI site present in plasmid sequences downstream of coat. These two DNAs were then joined by ligation to a vector fragment derived by Hind III-Bam HI cleavage of pMCT and introduced into *E. coli* by transformation. The resulting plasmids contain a duplication of the coat sequence, with the C-terminal amino acid of the upstream copy fused to amino acid 2 of the downstream sequence. This arrangement is identical to that found in the previously constructed p2CT-d113 [Peabody et al., 1996, Nucleic Acids Res 24(12):2352-9], but with two conservative amino acid substitutions to accommodate the introduction of the Bgl I site, whose presence at the junction simplifies single-chain dimer construction. The plasmid p2MCTK3 was constructed by a similar process. It provides a single-chain dimer with a unique Kpn I site in the AB-loop of its downstream half.

Protein Expression, Purification and Functional Assays

Figure 19:
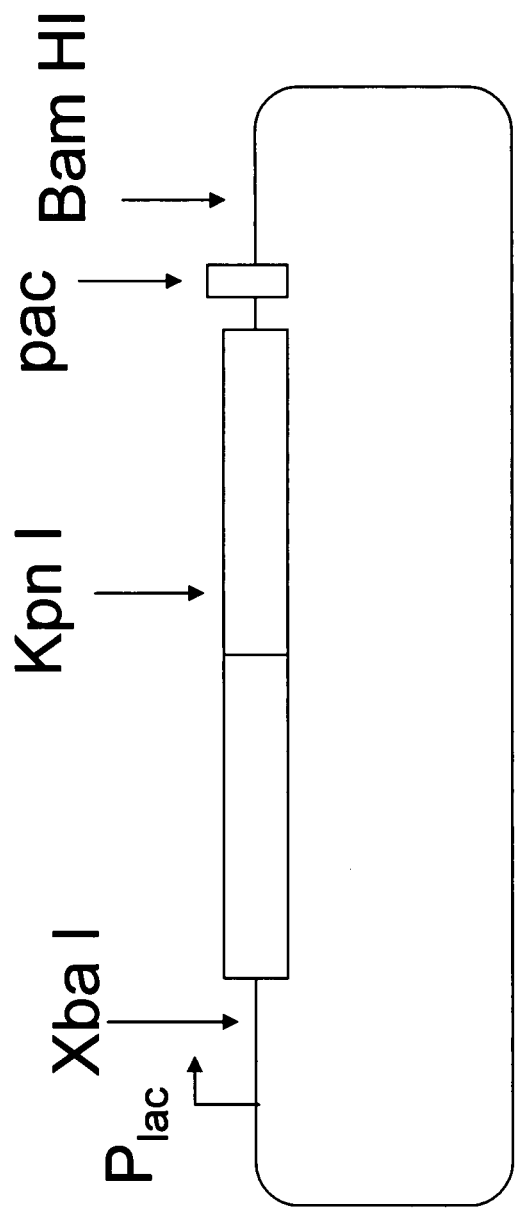
FIG. 19 shows a schematic diagram of p2MCTK3. This plasmid is a pUC119 derivative, contains an E. coli lac promoter which drives transcription of a single-chain dimer coat sequence with a unique KpnI site in codons 14 and 15 of the downstream copy of the coat sequence and has the translational operator (packaging signal) just downstream of coat gene.

To test the recombinant proteins for translational repressor activity, each plasmid was introduced into *E. coli* strain CSH41F⁻ containing the translational repression reporter plasmid called pRZ5 [Peabody, 1990, J Biol Chem, 265(10):5684-9] and plated on LB medium containing the β-galactosidase chromogenic substrate, 5-bromo-4-chloro-3-indolyl-β-D-galactoside (X-gal). To determine the expression levels of recombinant proteins and their solubilities, cell lysates from 1 ml overnight cultures were separated into soluble and insoluble fractions and subjected to SDS-gel electrophoresis (see Peabody, 1997, Arch. Biochem. Biophys. 347(1):85-92 for details). Contents of the gel were transferred to a nitrocellulose membrane and probed with rabbit anti-MS2 serum and alkaline phosphatase-conjugated goat anti-rabbit IgG antibodies. The coat proteins encoded in p2MCTK3 (see FIG. 19) p2MCTK-ECL2 and p2MCTK-V3 were purified to greater than 90% purity by chromatography in Sepharose CL-4B using methods described previously [Peabody, 1990, J Biol Chem, 265(10):5684-9].

Rapid assessment of a recombinant protein's ability to assemble into a VLP is performed by electrophoresis of sonicated cell lysates (from 1 ml overnight cultures) in gels of 1% agarose in 50 mM potassium phosphate, pH 7.5 [Peabody, 1993, Embo J 12(2):595-600]. Gels are stained with ethidium bromide to reveal the presence of VLPs, which contain host RNAs. The identity of the VLPs is then confirmed by transferring the contents of the gel to nitrocellulose and probing with rabbit anti-MS2 serum and an alkaline phosphatase-labeled second antibody.

Libraries of Random Sequence Peptides

To insert random DNA sequences encoding 6, 8 and 10-amino acid peptides into the AB-loop, the primers described below were used to amplify a coat fragment from pMCT in three different PCR reactions. Three different 5'-primers [called SEQ ID NO:. 22 $(NNY)_6$, SEQ ID NO: 23 $(NNY)_8$ and SEQ ID NO: 24 $(NNY)_{10}$] attach at codon 14 a Kpn I site and 6, 8 or 10 randomized codons of sequence NNY (where N=A,C,G, or T and Y=T or C). Each reaction employed a single 3'-primer that annealed downstream of a Bam HI site in the plasmid vector. The resulting PCR products were digested with Kpn I and Bam HI, gel purified and ligated to the similarly digested vector fragments of p2MCTK3 (see FIG. 19) or pMCTK2 (see FIG. 18). These were introduced by transformation into strain CSH41F$^-$ containing plasmid pRZ5 [Peabody, 1990, J Biol Chem 265(10):5684-9] and plated on LB medium containing X-gal. Control ligations containing only vector DNA gave rise to at least 1000-fold fewer colonies than those that contained an insert fragment. After overnight incubation at 37° C. the relative numbers of blue and white colonies obtained were determined by counting. Properly folded coat proteins repress translation of β-galactosidase and yield white colonies. From each library 24 white and 12 blue colonies were picked to two different 1 ml cultures in LB medium and grown overnight with shaking at 37° C. One set of cultures was used for plasmid isolation and DNA sequence analysis. The other was lysed by sonication and subjected to agarose gel electrophoresis as described above. VLPs were visualized by ethidium bromide staining and by blotting to nitrocellulose and probing with rabbit anti-MS2 serum and alkaline phosphatase-conjugated goat anti-rabbit IgG.

Packaging of Coat-Specific RNAs

Figure 21:
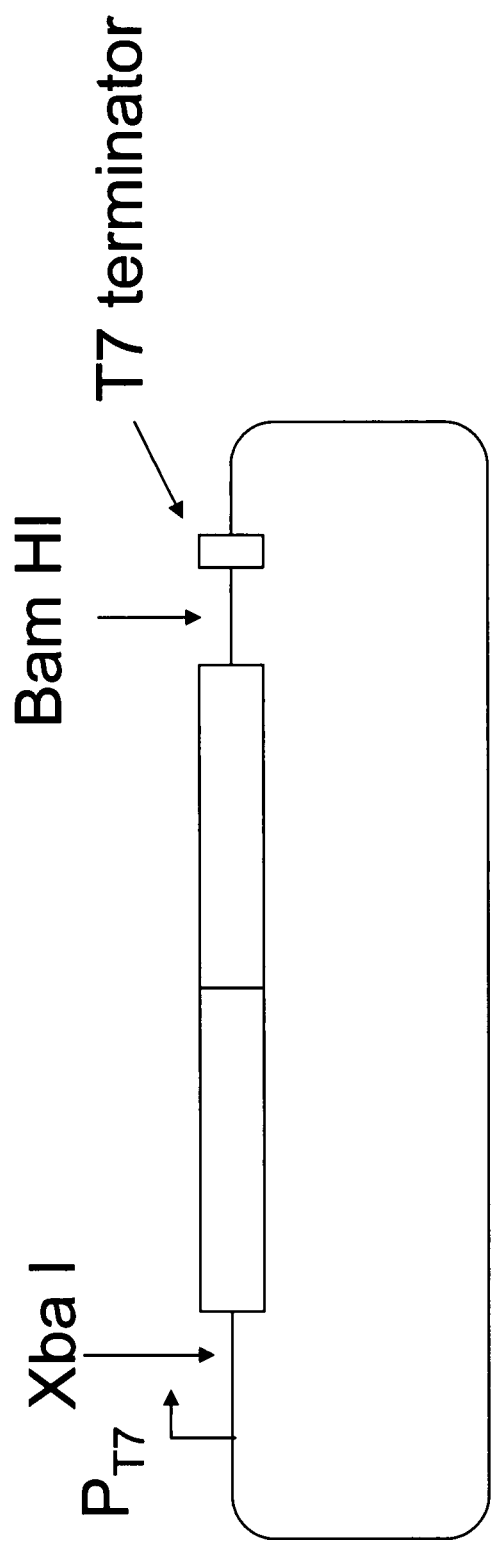
FIG. 21 shows a schematic diagram of pET2CT. pETCT contains a T7 promoter which drives transcription of the single-chain dimmer sequence and a T7 transcription terminator downstream of coat.

The Xba I-Bam HI fragments of plasmids pCT119 [Peabody, 1993, Embo J 12(2):595-600] and p2CTd1-13 [Peabody et al., 1996, Nucleic Acids Res 24(12):2352-9] were inserted into the T7 expression vector, pET3d [Studier et al., 1990, Methods in Enzymology 185:60-89]. Coat protein expression was induced by IPTG in bacterial strain BL21 (DE3)/pLysS using standard methods, and VLPs were extracted and purified by Sepharose CL-4B chromatography [Peabody, 1990, J Biol Chem 265(10):5684-9] followed by centrifugation to equilibrium in CsCl gradients (1.40 g/cc starting density) at 40,000 rpm in the SW50.1 rotor. RNAs were extracted from VLPs using phenol/chloroform and applied to a 1.5% agarose gel containing formaldehyde [Lehrach et al., 1977, Biochemistry 16:4743-4751]. The gel was blotted to nitrocellulose and probed with a coat-specific synthetic oligonucleotide (5'-CGAGTTAGAGCTGATC-CATTCAGCGACCCC-3') (SEQ ID NO:10) labeled at its 5'-end with $^{32}$P, Control RNAs were produced by transcription of pETCT (see FIG. 20) and pET2CTd1-13 (see FIG. 21) in vitro using T7 RNA polymerase.

Immunization and Characterization of Antisera

Antisera were prepared by inoculating C57B1/6 mice with 15 μg wild-type MS2 VLPs, 15 μg MS2-V3 VLPs, or 15 μg MS2-ECL2 VLPs. Mice were inoculated intramuscularly three times at 2-week intervals. Sera were collected prior to each injection and 2 weeks after the final boost. When adjuvant was used, antigen was diluted 1:1 IN COMPLETE Freund's adjuvant (CFA; initial injection) or incomplete Freund's adjuvant (IFA; subsequent boosts) immediately prior to the injection. All animal care was in accordance with the National Institutes of Health and University of New Mexico guidelines. Antibody titers were determined by ELISA using peptides corresponding to the target sequences. A V3 peptide (RIQRGPGRAFVTGK (SEQ ID NO: 11); synthesized by Commonwealth Biotechnologies, Chantilly, Va.) was conjugated to KLH using a carbodiimide crosslinker (Pierce). A cyclic peptide corresponding to macaque CCR5 ECL2 $(C_1D_2R_3S_4Q_5R_6E_7G_8L_9H_{10}Y_{11}T_{12}G_{13}$ SEQ ID NO: 25, in which Gly13 was linked to Asp2 through a dipeptide spacer; synthesized by Celtek Peptides, Nashville Tenn.) was conjugated to avidin using a heterobifunctional crosslinker (SMPH; Pierce). Conjugated peptides were immobilized (at 200 ng/well) onto Immulon II ELISA plates (Dynex Technologies, Chantilly, Va.) overnight at 4° C. and then wells were blocked with PBS plus 0.5% non-fat dry milk for 2 h at room temperature. Mouse serum was serially diluted in PBS-0.5% milk and applied to wells for 2.5 h at room temperature. Reactivity to antigen was determined using horseradish peroxidase (HRP)-labeled goat anti-mouse IgG (Jackson Immunoresearch, West Grove, Pa.) at a 1:2000 dilution in blocking buffer as a secondary antibody. Upon development, optical densities were read at 405 nm using an OpSys MR plate reader (Thermo Labsystems, Waltham, Mass.). $OD_{405}$ values that were greater than twice background (usually >0.080) were considered positive.

HIV neutralization was measured using the MAGI-CCR5 indicator cell line. These cells and the MAGI-CCR5 assay are described in more detail by Chackerian et al., 1997, J Virol 71(5):3932-3939. One hour prior to infection, dilutions of mouse sera were incubated with approximately 100 infectious HIV-$1_{LA1}$ virus particles in a total volume of 50 μL at 37° C. The virus-antibody mixture was then added to wells in a total volume of 200 μL in the presence of 10 μg/mL DEAE-Dextran (Sigma-Aldrich, St. Louis, Mo.). After 2 h at 37° C., virus and antibody were removed from each well and replaced with 0.5 mL of media. Two days after infection, cells were fixed, washed, and stained for β-galactosidase activity, as described previously [Kimpton et al., 1992, J Virol 66(4):2232-2239].

Binding of mouse serum IgG to native CCR5 was tested by flow cytometry. 293T cells were transiently transfected with a rhesus macaque CCR5-encoding expression vector [pc.Rh-CCR5; [Chen et al., 1997, J Virol 71(4):2705-14]]. Cells were detached from the monolayer using 5 mM EDTA and then washed three times in staining buffer (PBS plus 0.5% BSA). To remove antibodies that bound non-specifically to cells, sera was preincubated with untransfected 293T cells ($10^5$ cells for every 5 μL of sera) for 45 min at 4° C. Sera was removed from cells and then incubated with CCR5- or mock-transfected cells. Approximately $10^5$ cells were resuspended in 50111 of staining buffer plus 10 μL of mouse sera for 30 min at 4° C. After washing three times with staining buffer, cells were resuspended in 50 μl of staining buffer plus 250 ng of fluorescein isothiocyanate (FITC)-labeled goat anti-mouse IgG (Jackson Immunoresearch) and then incubated for 30 min at 4° C. As a control, cells were stained with secondary antibody alone or with a phycoerythrin (PE)-labeled anti-CCR5 monoclonal antibody (3A9; BD Pharmingen). Before analysis, cells were washed twice more with staining buffer and resuspended in 0.5 ml of staining buffer. Specific binding was measured relative to mock-transfected cells.

Results
Insertion of the ECL2 and V3 Peptides in the Coat Protein AB-Loop

The surface accessibility and regular geometric spacing of the AB-loop in the MS2 VLP make it an attractive site for the display of foreign peptides (FIG. 8). Two model peptides that in their natural environments are found in exposed loops have been inserted. One was derived from the V3 loop of the HIV envelope protein, gp120 of the lab-adapted strain, HIV-1$_{LA1}$. Its core sequence is relatively conserved among HIV isolates, and is a target of neutralizing antibodies [Laman et al., 1992, J Virol 66(3):1823-31]. The other peptide comes from the second extracellular loop (ECL2) of the macaque chemokine receptor, CCR5. In addition to its role in immune chemotaxis, CCR5 is a major coreceptor used by HIV to enter target cells. This particular sequence represents a region of ECL2 referred to as the undecapeptidyl arch (UPA) and is involved in HIV entry into cells [Misumi et al., 2001, J Virol 75(23):11614-20].

Figure 18:
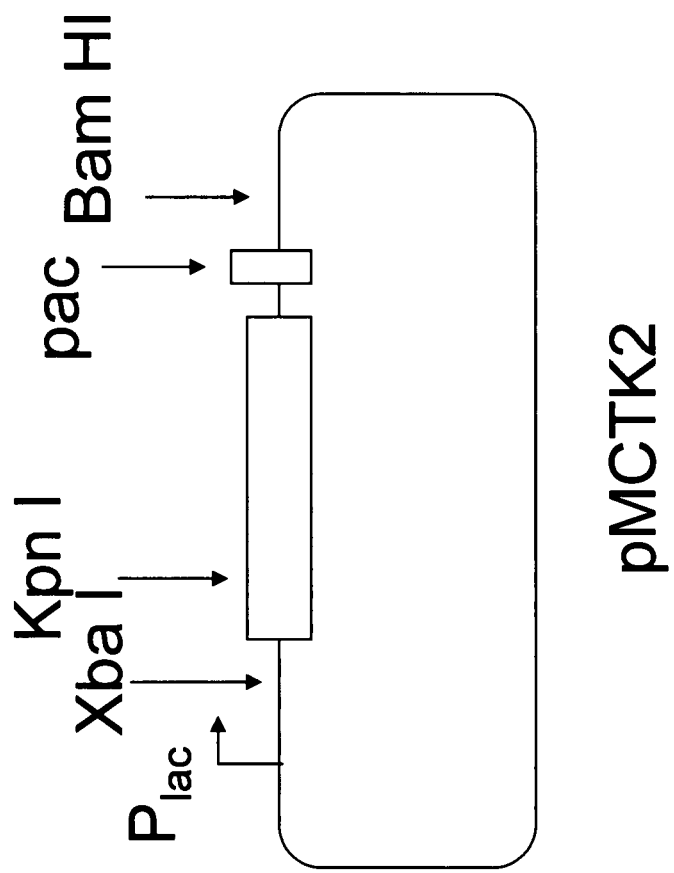
FIG. 18 shows a schematic diagram of pMCTK2 depicted in SEQ ID NO:20. This plasmid is a pUC119 derivative, contains an E. coli lac promoter which drives transcription of a coat sequence with a unique KpnI site in codons 14 and 15 and has the translational operator just downstream of coat gene.

To facilitate peptide insertion, the plasmid pMCTK2 was constructed (see FIG. 18). It is similar to the previously described pCT119 [Peabody, 1990, J Biol Chem 265(10):5684-9], but, following the example of Mastico et al. [Mastico et al., 1993, J Gen Virol 74 (Pt 4):541-8], was engineered to contain a Kpn I site in the AB-loop-encoding sequence (FIG. 10A). We then inserted duplex oligonucleotides (FIG. 10B) encoding 10-amino acid V3 and ECL2 peptides. Because insertion at Kpn I results in duplication of codons 14 and 15, the length of coat protein was actually increased by a total of twelve amino acids. The resulting plasmids, pMCTK2-ECL2 and pMCTK2-V3 express the recombinant coat proteins from the E. coli lac promoter. A Western Blot of the soluble and insoluble fractions of crude cell lysates (FIG. 11A) shows that the wild-type protein was abundantly produced in a predominantly soluble form, but neither of the recombinant proteins was present in detectable quantities. Their absence may be due to proteolytic degradation as a secondary consequence of a severe folding defect.

Functional tests confirm that the V3 and ECL2 recombinants are defective. Coat protein normally serves as a translational repressor, shutting off synthesis of the viral replicase by binding an 20-nucleotide RNA hairpin containing its ribosome binding site (the so-called translational operator). Fusing this sequence to the E. coli lacZ gene on the plasmid called pRZ5 [Peabody, 1990, J Biol Chem 265(10):5684-9] provides a simple means of assessing translational repressor activity of coat protein variants. Cells containing pRZ5 form white colonies on x-gal plates when they express functional coat protein, but make blue colonies they do not. Neither the ECL2- or V3-containing recombinant proteins inhibited β-galactosidase synthesis at all, indicating a complete failure to repress translation (Table I).

TABLE 1

| | Blueness on XGal |
|---|---|
| pUCter3 | +++ |
| pCT119 | − |
| p2MCTK3 | − |
| pCT-ECL2 | +++ |
| pCT-V3 | +++ |
| p2M-ECL2-2 | +++ |
| p2M-V3-2 | +++ |
| p2M-ECL2-1 | − |
| p2M-V3-1 | − |

The Folding Defects are Corrected in Single-Chain Dimers

FIGS. 8 and 9 show the structure of the coat protein dimer and illustrates the structural basis for construction of single-chain dimers. Note the physical proximity of the C-terminus of one subunit to the N-terminus of the other. It was previously demonstrated that genetic fusion of the two chains into single-chain dimers greatly protects the protein against the destabilizing effects of amino acid substitutions and chemical denaturants [Peabody, 1997, Arch Biochem Biophys 347(1):85-92, Mastico et al., 1993, J Gen Virol 74 (Pt 4):541-8, Peabody et al., 1996, Nucleic Acids Res 24(12):2352-9]. In an effort to suppress the defects imparted by the ECL2 and V3 insertions, we constructed two types of single-chain dimer; one has a foreign peptide in both AB-loops, and the other contains the peptide in only its C-terminal half (FIG. 10A).

The expression of the single-chain proteins was assessed by Western Blot (FIG. 11A). When present in both AB-loops, the single-chain dimer seems to revert partially the defects caused by the foreign peptides in the conventional dimer. The recombinant proteins are now detectable, but they are found predominantly as insoluble aggregates, suggesting that they are mostly misfolded. Their failure to correctly fold is also suggested by an inability to repress translation (Table 1). However, when the foreign peptides are incorporated into only the downstream copy of the single-chain dimer's two AB-loops the defect is fully corrected. The proteins are produced in normal amounts, are found mostly in the soluble fraction of the cell, and they repress translation just like wild-type (Table 1). The elution of the ECL2 and V3 single-chain proteins from Sepharose CL-4B at the same position as authentic MS2 virus is another indication that the recombinant proteins assemble normally into VLPs (FIG. 11B), and also provided a means to purify the ECL2 and V3 recombinant VLPs [Peabody, 1990, J Biol Chem 265(10):5684-9]. Analysis by SDS-polyacrylamide gel electrophoresis shows that the VLPs are nearly free of contaminating cellular proteins. Electrophoresis of the VLPs in an agarose gel under native conditions is shown in FIG. 11C. As expected of a properly assembled VLP, each contains RNA (it stains with ethidium bromide) and exhibits an altered electrophoretic mobility due to the charge differences conferred by the ECL2 and V3 peptides (FIG. 11B). Staining of the gel with the protein stain Coomassie Brilliant Blue shows the same pattern. The mobility of the capsid produced by the unmodified single-chain dimer (p2MCTK3—see FIG. 19) is slightly greater than that shown by the wild-type VLP produced from pMCTK, perhaps because subunit fusion reduces by half the number of positively charged N-termini, which happen to reside near the VLP surface.

Recombinant V3-VLPs were further characterized using a monoclonal antibody (mAb) (MAbIIIB-V3-13) that recognizes the V3 epitope and has HIV neutralizing activity [Laman et al., 1992, J Virol 66(3):1823-31]. MAbIIIB-V3-13 specifically bound to purified V3-VLPs immobilized on a ELISA plate, but not to wild-type MS2 VLPs or ECL2-VLPs (FIG. 12A), showing that the inserted V3 sequence is exposed on the surface of recombinant VLPs in a form competent for recognition by the monoclonal antibody.

Immunogenicity of the ECL2 and V3 Recombinants

The abilities of purified recombinant ECL2- and V3-VLPs to induce antibodies against the target sequences were assessed by immunization of C57B1/6 mice. Sera were tested for IgG antibodies specific for either the V3 or ECL2 peptides by end-point dilution ELISA. Mice immunized with V3-VLPs or ECL2-VLPs developed high titer ($>10^4$)

IgG responses against the corresponding peptide, but not against the heterologous peptide (FIG. 12B). No peptide-reactive antibodies were detected in sera from wild-type MS2 VLP-immunized mice. As with other VLP-based immunogens, high titer antibodies were induced without the use of exogenous adjuvants; coadministration of FA boosted IgG levels only slightly.

It was next determined whether induced anti-V3 antibodies bound to full-length native protein. Because monoclonal antibodies that bind to this region of V3 have HIV neutralizing activity [Misumi et al., 2001, J Virol 75(23):11614-20], we tested whether sera from V3-VLP immunized mice could inhibit HIV infection. Pooled sera from V3-VLP immunized mice, control sera, or two different HIV neutralizing monoclonal antibodies were preincubated with approximately 100 infectious HIV-$1_{LAI}$ particles, which were then used to infect an HIV indicator cell line (MAGI cells). Control sera from mice immunized with wild-type MS2 VLPs had no HIV neutralizing activity whereas sera from V3-VLP immunized mice neutralized HIV (~75% neutralization at a 1:10 sera dilution) (FIG. 12C). The more potent neutralizing activity displayed by the anti-V3 mAb (MAbIIIB V3-13) is consistent with the ~10-fold higher V3-peptide ELISA binding activity of this mAb relative to the V3-VLP sera.

The ability of ECL2-VLPs to elicit antibodies that bind native CCR5 was tested by flow cytometry. Macaque CCR5 was expressed on 293T cells by transient transfection with a rhesus macaque CCR5 expression vector (pc.Rh.CCR5), and the binding of mouse IgG was measured relative to mock-transfected cells. As shown in FIG. 12D, sera from ECL2-VLP immunized mice bound to CCR5-transfected cells (relative to mock-transfected cells) whereas sera from control mice did not, demonstrating that anti-ECL2 antibodies bind native CCR5.

Testing the Single-Chain Dimer's Tolerance of Random Peptide Insertions

A library of random 6-amino acid insertions in the AB-loop of pMCTK2 (wild-type coat) and of 6-, 8-, and 10-amino acids in the second AB-loop of p2MCTK3 (the single-chain dimer) was created. This was accomplished by insertion of 6, 8 or 10 copies of the sequence NNY, where N=any nucleotide, and Y=C or T. Random NNY triplets produce codons for 15 of the 20 amino acids, and although such libraries cannot encode lys, glu, gln, trp and met, they create considerable diversity while avoiding the introduction of stop codons. The libraries were introduced into strain CSH41F-/pRZ5 and plated on X-Gal plates where the ability of coat protein to repress translation of β-galactosidase resulted in the formation of white colonies. Failure to repress, on the other hand, gives blue colonies.

The results are shown in Table 2.

TABLE 2

| | Percent white colonies | |
|---|---|---|
| | pMCTK2 | p2MCTK3 |
| $(NNY)_6$ SEQ ID NO: 22 | 2 | 96 |
| $(NNY)_8$ SEQ ID NO: 23 | nd | 94 |
| $(NNY)_{10}$ SEQ ID NO: 24 | nd | 92 |

These results dramatically illustrate the importance of subunit fusion for successful folding. In the case of the pMCTK2 6-mer library only 2% of colonies were white, showing that only rarely was a 6-mer insertion tolerated in the AB-loop of the conventional dimer. On the other hand, in the single-chain dimer 96% of 6-mer, 94% of 8-mer, and 92% of 10-mer insertions gave functional translational repressors. From each of these libraries 12 blue recombinants were randomly selected for sequence analysis. It was found in the 6-mer and 8-mer libraries, that about half the defective clones (5/12 and 6/12, respectively) had frameshift mutations (presumably caused by occasional errors during synthesis of the NNY primers), or were the products of anomolous ligation events. One quarter (3/12) of the defective 10-mer clones also had frameshift mutations. Thus, in each library a significant percentage of repressor-defective clones were not the results of failure to tolerate peptide insertions, but had other defects.

Visual inspection of the small percentage of sequences that resulted in folding failures immediately led to the impression that they are enriched in hydrophobic amino acids. This intuition was confirmed when all the peptide sequences were joined together into a single 662-amino polypeptide, with the tolerated (from white colonies, residues 1-482) and non-tolerated sequences (from blue colonies, residues 483-662) grouped together. A Kyte-Doolittle hydrophobicity plot [Gasteiger et al., 2005, The Proteomics Protocols Handbook, ed. J. M. Walker, pp. 571-607; Kyte et al., 1982, Journal of Molecular Biology, 157:105-132] shows a distinct transition to higher average hydrophobicity at the white/blue junction (FIG. 13).

A number of white clones were picked from each of the 6-mer, 8-mer and 10-mer libraries and subjected to analysis of their abilities to support the synthesis of properly assembled VLPs. Sonicated cell lysates were subjected to agarose gel electrophoresis, and VLPs were visualized by ethidium bromide staining (upper half of each set in FIG. 14) and by a Western Blot probed stained with anti-MS2 serum and alkaline phosphatase-conjugated anti-rabbit IgG (lower half of each set. The mobilities of the recombinant VLPs are diverse, because, as sequence analysis shows, most of the inserted peptides contain at least one charged amino acid. Importantly, tolerance of insertions is high: 100% (21/21) of 6-mer clones, and 87% (20/23) 8-mer clones contained a detectable VLP, while the frequency of successful 10-mers was 80% (16/20).

MS2 VLPs Encapsidate Their mRNAs

Plasmids called pETCT and pET2CTd1-13 express wild-type coat protein and the single-chain dimer, respectively, from transcripts of predicted lengths of about 580 and 970 nucleotides, whose ends are specified by the T7 promoter and terminator sequences. VLPs were purified from bacteria, and their RNAs were extracted and subjected them to denaturing agarose gel electrophoresis [Lehrach et al., 1977, Biochemistry, 16:4743-4751]. The ethidium-bromide-stained gel (FIG. 15, left panel) shows that each VLP contains a dominant species that comigrates with RNA markers produced by T7 transcription in vitro of the same pETCT and pET2CTd1-13 plasmids. Three other RNAs were also run as molecular weight markers and as hybridization controls. Two were genome RNAs extracted from purified MS2 (3,569 nucleotides) and Qβ phages (4,220 nucleotides), and another, about 650 nucleotides long, was produced by transcription in vitro of a plasmid containing HCV core sequences. A Northern Blot probed with a $^{32}P$-labeled synthetic coat-specific oligonucleotide verifies the identities of the encapsidated RNAs; only RNAs expected to contain the coat sequence hybridize with the probe (FIG. 15, right).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A library of virus-like particles (VLPs) comprising a plurality of MS2 VLPs, wherein each particle of said library comprises a single chain dimer coat polypeptide having a random heterologous peptide inserted in the A-B loop of the downstream subunit of said coat polypeptide, wherein said random heterologous peptide is displayed on said VLP, wherein said random heterologous peptide is encoded by a polynucleotide that has 6, 8, or 10 copies of a NNY sequence, where N is adenine (A), Cytosine (C), guanine (G) or Thymine (T) and Y is cytosine (C) or thymine (T).

2. A kit comprising the library of VLPs according to claim 1.

* * * * *